United States Patent [19]

Jones et al.

[11] Patent Number: 5,028,733
[45] Date of Patent: Jul. 2, 1991

[54] PROSTAGLANDINS

[75] Inventors: Robert L. Jones; Norman H. Wilson, both of Edinburgh, Scotland

[73] Assignee: National Research Development Corporation, London, England

[21] Appl. No.: 449,720

[22] Filed: Dec. 12, 1989

Related U.S. Application Data

[62] Division of Ser. No. 143,506, Jan. 13, 1988, abandoned, which is a division of Ser. No. 807,442, Dec. 10, 1985, abandoned, which is a division of Ser. No. 349,084, Feb. 12, 1982, Pat. No. 4,596,823.

[30] Foreign Application Priority Data

Jul. 1, 1980 [GB] United Kingdom ................ 8021537

[51] Int. Cl.$^5$ ........................................... C07C 177/00
[52] U.S. Cl. .................................... 560/119; 546/290; 546/342; 548/170; 548/180; 548/217; 560/8; 560/17; 560/61; 560/100; 562/405; 562/431; 562/471; 562/490; 562/501; 564/98
[58] Field of Search ...................... 560/119, 8, 17, 61, 560/100; 562/50, 405, 431, 471, 490; 564/98; 546/290, 342; 548/170, 180, 217

[56] References Cited

FOREIGN PATENT DOCUMENTS 2310339 3/1976 France .

OTHER PUBLICATIONS

Eggelte et al., "Synthesis of 9,11-didoxy-9a-homoprostaglandin", Jour. of the Royal Netherlands Chem. Soc., 96/10, Oct. 1977, pp. 271-275.

*Primary Examiner*—Robert Gerstl
*Attorney, Agent, or Firm*—Nixon & Vanderhye

[57] ABSTRACT

Bicyclooctane and bicycloheptane prostaglandin intermediates have been synthesized.

19 Claims, No Drawings

PROSTAGLANDINS

This application is a division of Ser. No. 07/143,506, now abandoned, filed Jan. 13, 1988, which is a division of Ser. No. 06/807,442, filed Dec. 10, 1985, now abandoned, which is a division of Ser. No. 06/349,084, filed Feb. 12, 1982, new U.S. Pat. No. 4,596,823.

This invention relates to biologically active compounds and in particular to certain novel compounds exhibiting activity at thromboxane receptor sites.

Thromboxane $A_2$ ($TXA_2$), which is derived from arachidonic acid via prostaglandin $H_2$ ($PGH_2$), is implicated in several potentially noxious actions on various body systems, including platelet aggregation, bronchoconstriction and pulmonary and systemic vasoconstriction. Thus $TXA_2$ may be involved in the normal sealing of blood vessels following injury but in addition may contribute to pathological intravascular clotting or thrombosis. Moreover, the constrictor actions of $TXA_2$ on bronchiolar, pulmonary vascular and systemic vascular smooth muscle may be important in the development of several anaphylactic conditions including bronchial asthma. There is also some evidence to implicate $PGH_2$ and $TXA_2$ in the genesis of inflammation.

It is an object of the present invention to provide compounds having activity at thromboxane receptor sites, and most especially to provide compounds which are inhibitors of thromboxane activity and are therefore of interest in one or more areas of medical treatment including the treatment of thrombotic disorders, the treatment of anaphylactic disease states, and treatments utilising anti-inflammatory agents.

Accordingly the present invention comprises a compound of formula (I)

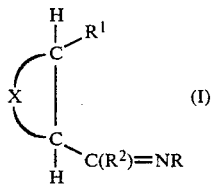

wherein

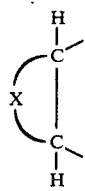

represents one of the divalent cyclic groups

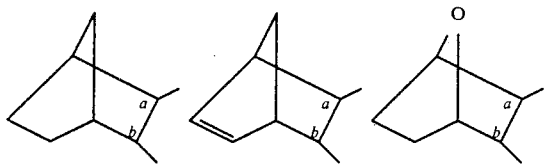

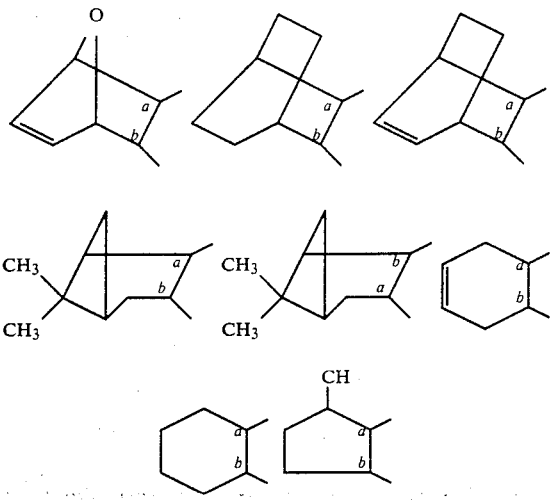

the letters a and b indicating in each case the points of attachment of the substituents $R^1$ and $C(R^2)=NR$, respectively, $R^1$ is a 6-carboxyhex-2-enyl group or a modification thereof as defined herein, $R^2$ is hydrogen, an aliphatic hydrocarbon group or an aliphatic hydrocarbon group substituted directly or through an oxygen or sulphur atom by an aromatic group, and R is a group $-OR^3$, $-OR^4$, $-A-R^3$ or $-N=R^5$ in which A is $-NH-$, $-NH.CO-$, $-NH.CO.CH_2N(R^6)-$, $-NH.SO_2-$, $-NH.CO.NH$ or $-NH.CS.NH-$ and wherein $R^3$ is an aliphatic hydrocarbon group, an aromatic group or an aliphatic hydrocarbon group substituted directly or through an oxygen or sulphur atom by an aromatic group, $R^4$ is an aliphatic hydrocarbon group which is substituted through an oxygen atom by an aliphatic hydrocarbon group which is itself substituted by an aromatic group, $R^5$ is an aliphatic hydrocarbon group, an aromatic group or an aliphatic hydrocarbon group substituted directly or through an oxygen or sulphur atom by an aromatic group, and $R^6$ is hydrogen, an aliphatic hydrocarbon group, an aromatic group or an aliphatic hydrocarbon group substituted directly or through an oxygen or sulphur atom by an aromatic group, with the proviso that when R is a group $-OR^3$, $-NH.COR^3$ or $-NH.CO.NHR^3$ then

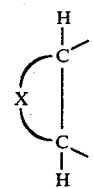

excludes the divalent cyclic groups

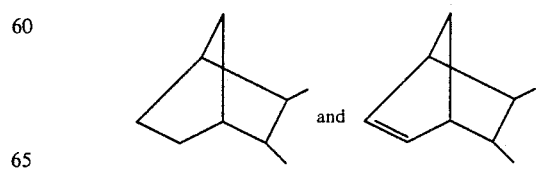

and pharmaceutically acceptable bioprecursors of such compounds of formula (I).

The various bridged ring systems indicated above may alternatively be represented in planar form, i.e. in the same order as

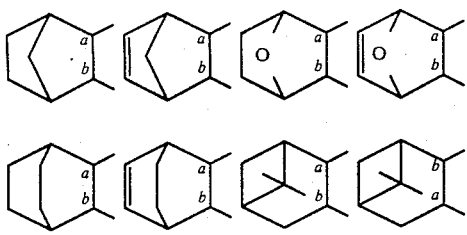

(the two free valencies in the centre of the last two formulae indicating methyl groups), but the more usual convention has generally been followed throughout the specification of representing these systems in non-planar form. It will be appreciated, however, that the compounds (I) may exist in various stereoisomeric forms, which are included within the scope of the invention, and in particular that each geometric isomer of a bridged ring compound (I) will exist in two enantiomorphic forms. These two forms will have the structure illustrated hereinbefore and the mirror image of that structure. Taking the vicinally disubstituted bicyclo [2,2,1] heptane ring system as an example, such pairs of enantiomorphs may be shown as follows (the rings being numbered according to the system used herein).

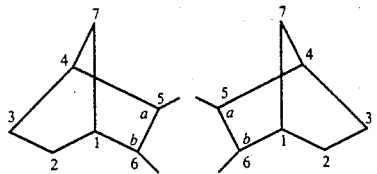

For the sake of added clarity it might be mentioned that alternative, equivalent, modes of showing these non-planar structures may be used, thus the right hand of the two formulae shown directly above is equivalent to

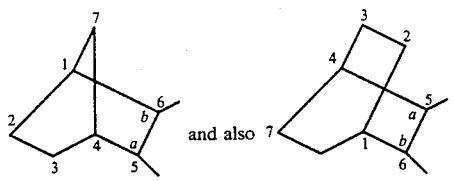

Certain of the compounds containing a modified 6-carboxyhex-2-enyl group act through the conversion of the modified group back to the unmodified group in vivo. In addition to such bioprecursors, the invention also extends in general to other pharmaceutically acceptable bioprecursors for the compounds described above, such a bioprecursor being a compound having a structural formula different from the active compound but which upon administration is converted thereto in vivo.

Modifications of the 6-carboxyhex-2-enyl group which may be made in compounds according to the present invention are of two types. Firstly, there are modifications which involve alteration of the 6-carboxyhex-2-enyl group by one, or where appropriate by a combination, of the following: (a) reduction of the double bond optionally accompanied by the replacement of a carbon atom at the 2,3 or even 1 position by a sulphur or particularly an oxygen atom; (b) alteration of the position of the double bond, for example to the 3, 4 position; and (c) shortening or lengthening of the carbon chain, particularly by one or two methylene groups and conveniently at the end of the chain adjacent to the carboxy group.

The second form of modification, which may if desired be combined with a modification of the first type, involves conversion of the carboxy group to a functional derivative including salts thereof. Functional derivatives described in the prostaglandin art are of particular interest, including esters such as alkyl esters, amides such as those containing the group —CONH-SO$_2$CH$_3$ and variants thereon, and salts with various physiologically acceptable cations. Specific examples of salts are those with an alkali metal such as sodium or with quaternary ammonium ions or amines such as tris (the symbol tris represents the compound 2-amino-2-hydroxymethylpropane 1,3-diol). As mentioned above, it will be appreciated that many of such compounds are in fact bioprecursors for the corresponding compound containing a carboxy group to which they are converted in vivo.

Examples of specific groups R$^1$ are —CH$_2$—CH=CH—(CH$_2$)$_3$CO$_2$H, —(CH$_2$)$_6$CO$_2$H and (CH$_2$)$_2$O(CH$_2$)$_3$CO$_2$H, and functional derivatives formed at the carboxy groups thereof.

Compounds in which the group R$^2$ is not hydrogen more usually contain aliphatic and araliphatic groups of the type described hereinafter in relation to the group R$^3$, aliphatic hydrocarbon groups substituted directly by an aromatic group and particularly unsubstituted aliphatic hydrocarbon groups being of most interest. The size of the group R$^2$ can however influence the ease with which the compounds may be prepared and R$^2$ is preferably either hydrogen or one of the smaller alkyl groups, for example of 1 to 3 carbon atoms, in substituted form, or particularly in unsubstituted form, for example ethyl and especially methyl. When the group R$^2$ contains an aliphatic hydrocarbon group directly substituted by an aromatic group, then it is preferred that the aromatic group is not attached to a carbon atom of the aliphatic group which is itself attached directly to the carbon atom of the group C(R$^2$)=NR. Thus, for example, a 2-phenylethyl group is preferred to a 1-phenylethyl or phenylmethyl (benzyl) group. Good levels of activity have been achieved with compounds in which R$^2$ is one of hydrogen, ethyl and especially methyl. The increase in activity resulting from the presence of a group R$^2$ which is methyl rather than hydrogen has been found to be particularly marked in the case of compounds (I) containing a group R of the form —NH.CO.NHR$^3$ or —NH.CS.NHR$^3$.

Among the groups C(R$^2$)=NR, those which terminate in a group R$^3$ are of particular interest. As indicated, the group R$^3$ can be of various forms. Aliphatic hydrocarbon groups constituting R$^3$ may conveniently be of one to five, six, seven, eight, nine, ten or even more carbon atoms, being, for example an alkyl group and including branched or unbranched acyclic alkyl groups such as methyl, ethyl, propyl, butyl, amyl, etc., cyclic alkyl groups such as cyclopentyl, cyclohexyl etc., and also combinations thereof such as cyclohexylmethyl etc.

Aromatic groups constituting R$^3$ are of greater interest than the unsubstituted aliphatic hydrocarbon groups and may be hydrocarbon or heterocyclic groups which may be unsubstituted or substituted. Moreover, the term 'aromatic group' as used herein extends to groups derived from ring systems having aromatic properties but in which the π-electron system is not fully delocalised over the entire ring system, such groups including those derived from fluorene, dihydrobenzoxazole, dihydrobenz thiazole, N-methyldihydrobenzothiazole, and 1,2,4,5-dibenzocycloheptane. The heterocyclic groups which conveniently contain one, two or more, similar or different nitrogen, oxygen or sulphur atoms, are more generally linked through a carbon atom so that, in the case of a pyridyl group, pyrid-2-yl, pyrid-3-yl and pyrid-4-yl are of particular interest. Moreover, in the case of those groups containing one or more benzene rings together with one or more non-benzenoid rings, such as those derived from fluorene and its cyclohexyl and cycloheptyl analogues, and from benzothiazole, dihydrobenz, N-methyldihydrobenzthiazole and their benzovazole analogues, and, linkage of the group is more usually effected through a non-benzenoid ring.

Among the aromatic groups constituting $R^3$, aromatic hydrocarbon groups, for example napthyl and particularly phenyl are, however, generally of rather greater interest than heterocyclic groups. Both the aromatic hydrocarbon and the heterocyclic groups may be substituted, by one or more of various types of substituent, particularly by alkoxy groups, for example those containing alkyl groups of 1,2,3 or more carbon atoms as described above and especially methoxy, and by substituents being or containing a halogen residue, for example chloro and especially fluoro, and also halogen substituted alkyl groups such as $CF_3$. Examples of other substituents are sulphamoyl groups which may optionally be N-substituted, amino groups which may be free or substituted, for example dimethylamino, hydroxyl, nitro, and alkyl groups, for example of 1 to 3 carbon atoms or otherwise as described above, etc. Substitution may be present at one or more of the ortho, meta and para positions of a phenyl ring or at a combination of two or more such positions (including two similar positions), for example at the 2 and 4 positions. Substitution and the position of substitution, for example by alkoxy groups and groups being or containing a halogen, may have a definite effect upon the level of activity of a compound.

Also of considerable interest, are groups $R^3$ which are aliphatic hydrocarbon groups substituted directly or through a sulphur or particularly an oxygen atom by an aromatic group. The aliphatic groups may be of a similar size to those described above but preferably comprise an acyclic group, conveniently of three carbon atoms, particularly of two carbon atoms and especially of one carbon atom, although this acyclic group may carry a cyclo-alkyl group as well as an aromatic group. Preferred acyclic groups thus take the form of unbranched alkylene groups such as methylene, ethylene or propylene which link the group $C(R^2)=N-$ and the aromatic group, or corresponding trivalent groups of similar size. Similar aromatic hydrocarbon and heterocyclic residues are generally of interest for attachment to the aliphatic groups as have already been described above, the aromatic hydrocarbon groups again generally being of rather more interest than the heterocyclic groups. Heterocyclic groups, where used, are of most interest in this context when linked to the aliphatic hydrocarbon group through a hetero atom such as in pyrid-1-yl. Substitution of an aliphatic hydrocarbon group, particularly terminally, by two or even three aromatic groups, for example phenyl, is of particular interest, whilst also of interest are acyclic groups carrying terminally both an aromatic group, for example phenyl, and a cyclo-alkyl group, for example cyclohexyl. Other substituted aliphatic hydrocarbon groups of especial note are those which are substituted through a sulphur or particularly an oxygen atom, although in this case the aliphatic hydrocarbon group is conveniently of at least two carbon atoms in the case of some forms of group $C(R^2)=NR$ in view of the relative instability of the linkages $-O-CH_2-S-$ and $-O-CH_2-O-$.

When the group $R^3$ is or contains a substituted aromatic group, some positions of substitution may be of more interest than others in particular cases. Thus, for example, when $R^3$ is a substituted benzyl group the order of interest is often o~p>m, when $R^3$ is a substituted phenyloxyethyl group it is o>m>p, and when $R^3$ is a substituted phenyl group it is m~p>o. It will be appreciated that, particularly when two positions are of similar interest, it may be of value to have a substituent at each position as when the group $R^3$ is 3,4-dimethoxyphenyl.

Among the various groups R which terminate in a group $R^3$, those of particular interest are the groups in which R is a group $-OR^3$ or a group $-A-R^3$ in which A is $-NH.CO-$, $-NH.SO_2-$, $-NH.CO.NH-$ or $-NH.CS.NH-$. Very good levels of activity have been obtained with compounds in which R is a group $-OR^3$ or particularly a group $-NH.CO.NHR^3$ and especially a group $-NH.CS.NHR^3$. Among various groups R terminating in a group $R^3$, those in which $R^3$ is an aliphatic hydrocarbon group are perhaps of rather less interest than the others, groups $R^3$ which are aliphatic hydrocarbon groups substituted directly or through an oxygen or sulphur atom by an aromatic group being of somewhat greater interest when R is a group $-OR^3$ and groups $R^3$ which are aromatic groups being of somewhat greater interest when R is a group $-A-R^3$. It will be appreciated, however, that this is only a broad generalisation, so that, for example, one group $R^3$ containing an aliphatic hydrocarbon group substituted by an aromatic group which is of some interest in groups $-A-R^3$ is that consisting of an ethyl group substituted at the 1-position by a napthyl group, for example a napth-1-yl group. The reagent $H_2N.NH.CO.NHCH(CH_3)$-napth-1-yl, which may be used to prepare compounds (I) containing such a group, is of particular interest since it contains an asymmetric carbon atom and may be obtained in optically active form. Examples of specific groups $R^3$ are:

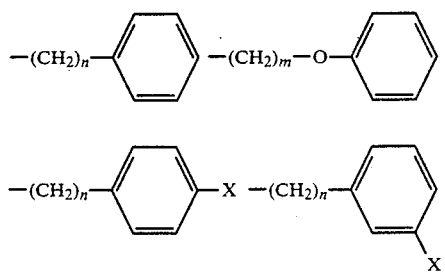

-continued

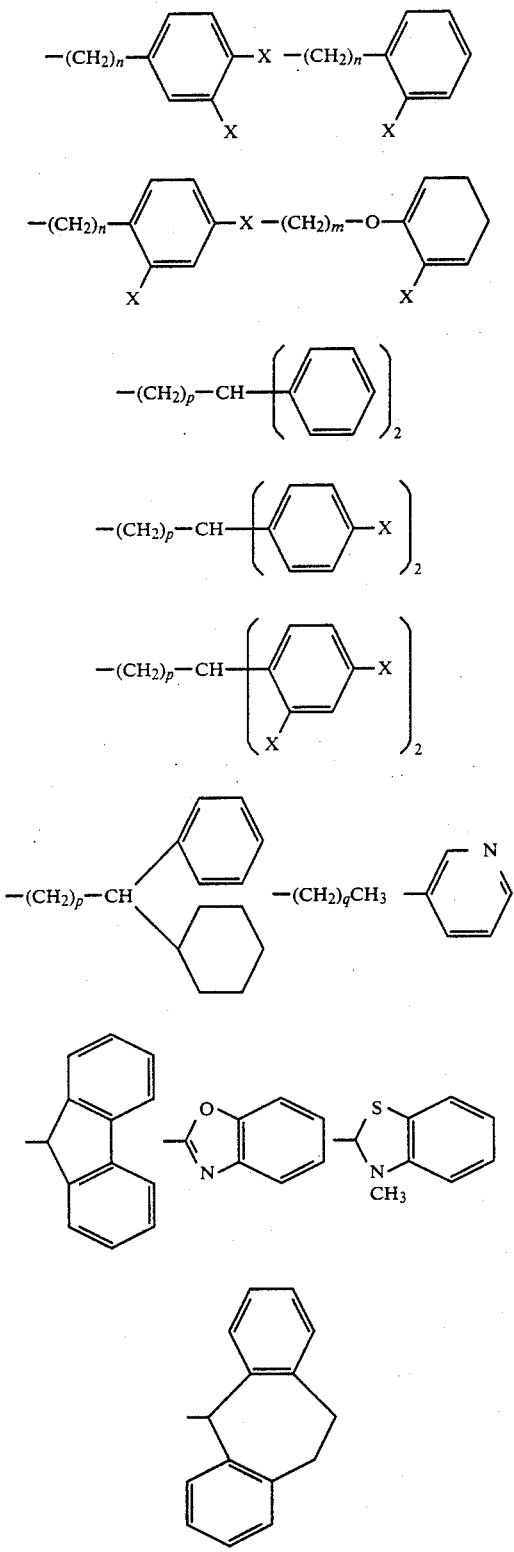

wherein n=0, 1, 2 or 3, m=1, 2 or 3 (but particularly 2 or 3 in some cases as discussed above), p=0, 1 or 2, q=1, 2, 3, 4 or 5 and X=OCH$_3$, Cl, F, CF$_3$ or CH$_3$ (preferences between ortho, meta and para substitution in the cases where n is 0 or not being indicated hereinbefore).

In addition to compounds containing 0-substituted oxime groups of the C(R$^2$)=NOR$^3$ type which are discussed above, the invention also includes compounds containing 0-substituted oxime groups of the type C(R$^2$)=NOR$^4$. The group R$^4$, as indicated above, is an aliphatic hydrocarbon group which is substituted through an oxygen atom by an aliphatic hydrocarbon group which is itself substituted by an aromatic group and preferences as regards both aliphatic hydrocarbon groups and the aromatic group are broadly as expressed above in the case of the group R$^3$. In particular, the aliphatic hydrocarbon group attached to the oxime oxygen atom is preferably of more than one carbon atom, for example being of three or particularly two carbon atoms, whilst the aliphatic hydrocarbon group substituted by an aromatic group is preferably of one to three carbon atoms, for example one carbon atom. This latter aliphatic hydrocarbon group may conveniently be terminally substituted by one, two or even three aromatic groups although two or only one aromatic groups are preferred and these may conveniently be phenyl groups or substituted phenyl groups as described above in relation to R$^3$.

As well as compounds (I) containing a group C(R$^2$)=NR terminating in a monovalent group R$^3$ or R$^4$ other compounds (I) of some interest contain a group C(R$^2$)=NR in which R is —N=R$^5$, R$^5$ being a divalent organic group as defined above. Unsubstituted and substituted aliphatic hydrocarbon groups R$^5$ most usually are groups similar to those described above in relation to R$^3$ but which contain two free valencies at the point of linkage. In the case of groups R$^5$ which are aromatic groups it will be appreciated that there will not be such a close correspondence to the groups R$^3$ described above as these aromatic groups, because of their divalent nature, generally cannot derive from many of the aromatic systems described above in which the $\pi$-electrons are fully delocalised over the whole ring system, such as those comprising a single benzene or pyridine ring. Such aromatic groups constituting R$^5$ are therefore usually of the type described hereinbefore in which the $\pi$-electron system is not fully delocalised over the entire ring system and, indeed, this type of residue is one of those preferred in the case of R$^5$, specific preferences among such types of aromatic group being as discussed above in relation to R$^3$. Another preferred type of group R$^5$ is a methylene group in which both hydrogen atoms are substituted by an aromatic group, for example such as phenyl, so that the double bonds of the C(R$^2$)=N—N=C< system are in conjugation with the aromatic system. Examples of specific groups R$^5$ are:

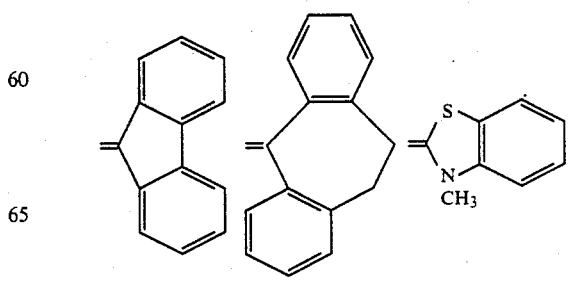

-continued

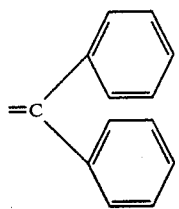

As regards the group $R^6$ which constitutes a part of groups —A—$R^3$ of the specific type

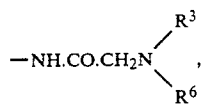

the preferences among aliphatic, aromatic and araliphatic groups $R^6$ generally correspond to those indicated above for $R^3$ although aliphatic hydrocarbon groups are of rather more interest than is generally the case and, with the araliphatic groups, direct substitution by an aromatic group is preferred to substitution through an oxygen or sulphur atom. Moreover, an important additional alternative is for $R^6$ to be hydrogen. Conveniently the group

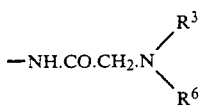

either contains a group $R^6$ which is identical to the group $R^3$, for example both being an unsubstituted aliphatic hydrocarbon group or one substituted directly by an aromatic group, or a group $R^6$ which is hydrogen. Thus, specific examples of the larger group are —NH.CO.CH$_2$.N(CH$_2$C$_6$H$_5$)$_2$ and —NH.CO.CH$_2$N(C$_2$H$_5$)$_2$ or —NH.CO.CH$_2$NH(CH$_2$C$_6$H$_5$).

As indicated above, compounds according to the present invention may contain, in the order shown previously, one of the following types of ring system: bicyclo [2,2,1] heptane, bicyclo [2,2,1] hept-2Z-ene, 7-oxabicyclo [2,2,1] heptane, 7-oxa-bicyclo [2,2,1] hept-2Z-ene, bicyclo [2,2,2] octane, bicyclo [2,2,2] oct-2Z-ene, 6,6-dimethyl-bicyclo [3,1,1] heptane, cyclohexene, cyclohexane and hydroxycyclopentane. The 6,6-dimethyl-bicyclo [3,1,1] heptane ring system, unlike the others, may be substituted in either of two ways, corresponding to reversal of the substituents shown at the a and b positions. It will be appreciated that the bridged ring systems present in compounds according to the present invention show a range of degrees of asymmetry. Thus, the 6,6-dimethyl-bicyclo [3,1,1] heptane ring system is sufficiently asymmetric for reversal of the substituents at the a and b positions to result in a different structural isomer, and thus a different compound (I), both types of compound (I) containing the 6,6-dimethyl-bicyclo [3,1,1] heptane ring system being covered by the present invention. In the case of the bicyclo [2,2,1] heptane and bicyclo [2,2,1] hept-2Z-ene ring systems and their 7-oxa analogues, however, reversal of these substituents would merely provide a structure which represents an alternative stereoisomer, the invention, as has previously been indicated, extending to the compounds (I) in their various stereoisomeric forms. The situation with the bicyclo [2,2,2] oct-2Z-ene ring system is analogous to that pertaining in the case of its 7-membered analogue but the bicyclo [2,2,2] octane ring system has a sufficient degree of symmetry for such reversal of the a and b substituents to give the same compound (I) of identical stereochemistry. Among these ring systems, the bridged ring systems are of particular interest and of these the bicyclo [2,2,2] octane and the 6,6-dimethyl-bicyclo [3,1,1] heptane ring substituted at the 2-position by the group C(R$^2$)=NR rather than the group R$^1$ may be mentioned particularly. Among those bridged ring systems which may be saturated or unsaturated, the former are usually preferred, particularly in the case of the compounds containing an oxygen bridging group, as unsaturation generally confers lower stability whilst the level of biological activity is generally substantially similar.

It will be appreciated that the structures of the compounds described above provide various opportunities for the occurrence of stereoisomerism. The substituent groups R$^1$ and C(R$^2$)=NR may be in the cis or trans relationship to each other, compounds of the latter configuration being preferred. Moreover, when the ring system is one which is bridged or contains a hydrogen substituent then, in most cases, different isomers will exist which vary according to the way in which the substituent groups R$^1$ and C(R$^2$)=NR are disposed in relation to the bridging groups or the substituent. Isomers of particular interest are shown below in one of the two enantiomorphic forms which can exist in each case, the other enantiomorph having a structure which is the mirror image of that shown. The unsaturated ring system is illustrated where the ring system may be saturated or unsaturated and the symbol B represents —CH$_2$— (position 7), —O— (position 7) or —CH$_2$CH$_2$—(positions 7 and 8). As indicated above, the bicyclo [2,2,2] octane system possesses a greater degree of symmetry than the other bridged ring systems, as the two bridging groups attached together at the bridge positions (1 and 4) are identical, both being —CH$_2$CH$_2$—. In this case therefore, although the trans isomer is preferred and can exist in two enantiomorphic forms, the endo, exo type isomerism which can occur with the other bridged ring systems cannot arise.

It will be seen that in the structures shown below the numbering applied herein to the various positions of the ring system has been indicated. It should be noted that the system of numbering adopted for the bridged ring systems which can exist in both saturated and unsaturated form is chosen so that the double bond in the unsaturated ring system receives the lowest number possible (2), the substituents R$^1$ and C(R$^2$)=NR then being at the 5 and 6 positions respectively. For conformity, a similar system of numbering is followed for the analogous saturated ring systems, the substituents again being described as at the 5 and 6, rather than the 2 and 3, positions as in the 6,6-dimethyl [3,1,1] heptane system.

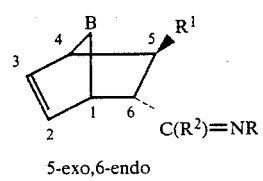 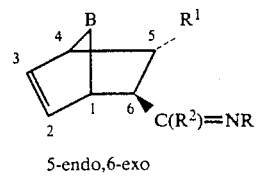

5-exo,6-endo  5-endo,6-exo

-continued

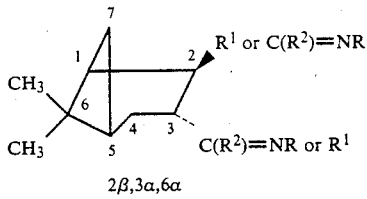

2β,3α,6α

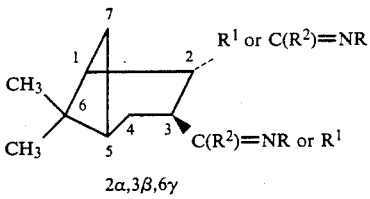

2α,3β,6γ

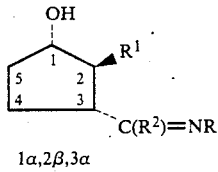

1α,2β,3α

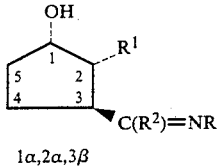

1α,2α,3β

Among the isomers illustrated above in two forms, one form is usually preferred to a somewhat greater extent than the other. In the case of the 5-exo, 6-endo and 5-endo, 6-exo isomers the latter is most usually preferred except that in the case where B is —O— then the 5-exo, 6-endo isomer is also of considerable interest. In the case of the 2β, 3α, 6α and 2α, 3β, 6α isomers the latter is of most interest. [The convention applied herein for naming the compounds (I) containing a 6,6-dimethyl-bicyclo [3,1,1] heptane ring system is the use of α and β to indicate the directions in which the substituents at the 2- and 3-positions are directed. In the designations used above the position of the bridging carbon atom at position 6 has for simplicity also been indicated by an α or a β (the position of the gem dimethyl groups at the 6-position is dictated by that of the carbon atom to which they are attached)].

Where the substituent $R^1$ is a 6-carboxyhex-2-enyl group or a group modified therefrom but still containing the double bond, then the configuration about this bond is preferably cis (Z) rather than trans (E). In the other substituent $C(R^2)$=NR, syn and anti isomerism is possible about the carbon-nitrogen double bond but the isomers may often be readily interconvertible at room temperature and thus difficult to separate, existing as a mixture which shows biological activity that may, however, derive predominantly from one isomer. In addition to the foregoing isomerism, as indicated previously the compounds of the present invention will in most cases additionally be resolvable into enantiomorphic forms and one among these may be preferred by virtue of biological activity or physical properties. Single enantiomers may be obtained either by the use of an optically active starting material or by resolution of a pair of enantiomorphs.

Specific compounds according to the present invention include the various compounds described in the Examples as well as the analogues thereof in which a 6-carboxyhex-2Z-enyl group is replaced by a 6-carboxyhexyl group and/or the group $R^2$ is the other two of the groups hydrogen, methyl and ethyl than the one appearing in the specific compound in question, for example the compound

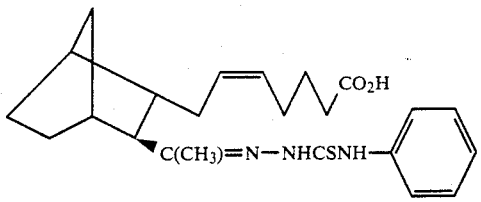

Compounds of formula (I) according to the present invention may be prepared by reacting a compound of formula (II)

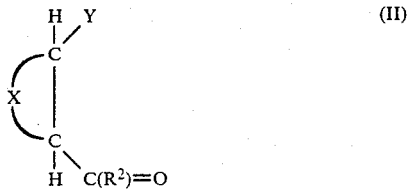

with a reagent $ZNH_2$, Y being either $R^1$ as defined above for compound (I) or a precursor for $R^1$ and Z being either R as defined above for compound (I) or a precursor for R, and the other symbols being as defined for compound (I), and where appropriate converting the group Y and/or the group Z in the resultant product into the groups $R^1$ and R, respectively, of the compound (I). Preferably Z and conveniently also Y correspond to the corresponding groups R and $R^1$ in the compound (I).

A convenient form of intermediate for the preparation of all the various compounds (I) according to the present invention is a compound of formula (III) in which the symbols have the meaning indicated for formula (II). When the desired compound (I) contains a substituent $C(R^2)$=NR in which $R^2$ is hydrogen then the compound of formula (III) corresponds to that of formula (II) and is itself reacted with the reagent $ZNH_2$ to give the compound (I) either directly or after modification of Y and/or Z. When the desired compound of formula (I) contains a substituent $C(R^2)$=NR in which $R^2$ is not hydrogen, the compound of formula (III) may conveniently be reacted with a Grignard reagent of the form $R^2MgHalogen$, followed by oxidation of the secondary alcohol of formula (IV) so formed, for example using Jones reagent, and the resulting compound of formula (II) containing the desired group $R^2$ reacted with the reagent $ZNH_2$ as indicated previously

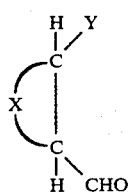

(III)

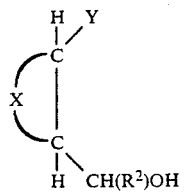

(IV)

It will be appreciated that the various intermediates as just described are included by the present invention in view of their value in the preparation of the compounds (I). The preparation of such compounds of formula (III) is described in detail in the Examples for various of the ring systems and the synthesis of a compound (III) containing the bicyclo [2,2,1] heptane ring system is shown schematically at the end of the examples. The 5-endo, 6-exo isomer is illustrated throughout the scheme in one enantiomeric form, although as explained hereinafter the product obtained by this route is racemic and it is also possible that some minor contamination with other isomers may occur. It will be appreciated that the proportion of such contaminants does not necessarily depend upon the stereo-chemical nature of the intermediates in earlier stages of the synthesis. Thus certain compounds are capable of epimerisation under particular conditions and the compounds (III) in particular can undergo an epimerisation involving the formyl group at the time when these products are generated by the action of acid on the acetal.

The corresponding 7-oxa-bicyclo [2,2,1] heptane and bicyclo [2,2,2] octane compounds (III) are prepared by relatively similar routes particularly in the case of the latter compound. In these cases, however, it is preferred to use an acetal prepared from ethylene glycol rather than ethanol since the equilibrium of the reaction with ethanol does not lie sufficiently towards the ring closed form. Preparation of compounds (III) in the case of the remaining ring system is readily achieved by modification of these syntheses. Thus the unsaturated bicyclic ring systems bicyclo [2,2,1] hept-2Z-ene, 7-oxa-bicyclo [2,2,1] hept-2Z-ene and bicyclo [2,2,2] oct-2Z-ene may be prepared by omitting or modifying the reduction step which converts the unsaturated ring system which is produced initally in each case to the corresponding saturated ring system, for example by omitting the catalytic reduction employing $H_2/Pd$ in the route shown schematically. [The synthesis of the bicyclo [2,2,1] hept-2Z-ene compound of formula (III) is described in detail in U.K. Patent Application Nos. 8000278 and 8000279, published under the serial numbers 2039480 and 2039909 respectively, and also in the corresponding applications filed in other countries.] Compounds (III) containing the cyclohexane ring system may be obtained by the introduction of a $H_2/Pd-C$ reduction step, such as is illustrated in the schematic route, into the synthesis of the equivalent cyclohexane compound, reducing the cis-4,5-bis-hydroxymethylcyclohex-1-ene to give cis-4,5-bis-hydroxymethylcyclohexane before proceeding with the formation of the monobenzyl ether. Alternatively, cyclohexane 1,2-dicarboxylic acid anhydride may be used as the starting material.

Other stereoisomers are obtainable by modified routes. Thus, for example α-pinene may be obtained in both optically active forms thus providing a route to (+)-nopol and (+)-myrtenol as alternative starting materials for use in the routes described in Examples 7, 8 and 9. Also, in the case of the 7-oxa-bicyclo [2,2,1] heptane compounds and their ring unsaturated analogues other routes described in the literature provided may be used directly or with modifications to produce other stereoisomeric forms, for example the 5-endo, 6-exo isomer, of the intermediate compound of type (III) containing a 6-carboxyhex-2'Z-enyl or 6-carboxyhexyl substituent $R^1$ (Eggelte et al, J. C. S. Perkin I, 1978, 980 and Sprague et al, Advances in Prostaglandin and Thromboxane Research, 1980, 6, 493). Alternatively, the route described herein may be modified, the hydroxymethyl/acetal of Example 6(4) being used to build up the $R^1$ substituent from the acetal group and the hydroxymethyl group being converted to the $C(R^2)=O$ group and thus the $C(R^2)=NR$ group thereby producing the alternative 5-endo, 6-exo isomer. One procedure for doing this involves protection of the alcohol group, for example as an ester, removal of the acetal and reaction of the aldehyde group with a methoxymethyl phosphonium ylide. Following this the group $R^1$ can be built up further and the hydroxymethyl group reduced to a formyl group.

When the group $R^1$ in the desired compound of formula (I) contains a free carboxy group then the group Y in the compound of formula (II) may similarly contain a free carboxy group or may, as illustrated in the schematic route, contain a carboxy group in protected form, for example as an ester and particularly as the methyl ester which may conveniently be formed with diazomethane. Following reaction with the reactant $Z.NH_2$ such a protecting group may then be removed, for example by de-esterification using $KOH/CH_3OH/H_2O$. Such protection will generally lead to a slightly greater overall yield of the compound (I) from the compound (II).

The reactants $ZNH_2$ are most usually of the form $RNH_2$ and may be prepared by various procedures known in the art and illustrated in the Examples, the procedures illustrated generally being applicable to a variety of forms of groups $R^3$, $R^4$ and $R^5$ in R. Thus, for example, the reagents $H_2N.NH.CO.R^3$ may conveniently be prepared by the reaction of hydrazine with the corresponding ester for example the ethyl ester, $R^3.CO_2C_2H_5$. The reagents $H_2N.NH.CO.NHR^3$ may be prepared by the reaction of hydrazine with the corresponding N-substituted carbamate, for example the ethyl carbamate, $R^3NHCO_2C_2H_5$ (particularly for the preparation of phenyl semicarbazide) or more often in general with the corresponding isocyanate, $R^3NCO$.

Reagents $H_2N.NHCSNHR^3$ may be prepared very conveniently through the reaction of the corresponding primary amine $R^3NH_2$ with carbon disulphide in the presence of dicyclohexylcarbodiimide, followed by reaction of the resulting isothiocyanate, $R^3NCS$, with hydrazine. Reaction between the compound of formula (II) and the reactant $ZNH_2$ is often effected either with its HCl salt in pyridine or with the free base in a neutral solvent, for example tetrahydrofuran or dioxane, some degree of heating often being used as shown in the Examples. Particular care may often be needed when using certain reactants $H_2N.NHR^3$ (often obtainable by $H_2/Pd$ reduction of $H_2N.N=R^5$) to avoid oxidation with formation of a compound containing a group $C(R^2)=N-N=R^5$ rather than one containing a group $C(R^2)=N-NHR^3$. This problem is particularly likely to be encountered where $R^3$ is a methyl group substituted by two aromatic groups, for example where $R^3$ is a diphenylmethyl or a fluoren-9-yl group and groups not of this type are accordingly preferred in the case of groups R of type $-NHR^3$.

It will be appreciated that certain of the reagents $Z.NH_2$ are novel compounds and that these are included within the scope of the present invention.

Modification of the 6-carboxyhex-2-enyl group may be effected through the initial introduction of a modified group or by modification of this group during or at the end of the synthesis, ester formation conveniently being effected, for example, at the stage indicated hereinbefore and amides similarly being prepared by conventional procedures. Indeed, the procedures for effecting the various modifications indicated above will be apparent from the considerable literature existing on prostaglandin chemistry. Thus, for example, in the case of a saturated ring system, where, as is the case in the schematic route, a precursor of structure

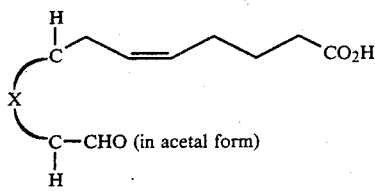

is involved in the synthesis of compounds containing a 6-carboxyhex-2-enyl group, then a convenient route to the analogues containing a 6-carboxyhexyl group involves the reduction of this precursor, for example with $H_2/Pd$-C. The preparation of compounds containing a 6-carboxyhexyl group in this manner is described in the application No. 6B2039909A. Where the synthetic route initially involves compounds containing the corresponding unsaturated ring it may be possible, if desired, to reduce both the ring and chain double bonds at this stage in one step. In the case of other ring systems, particularly the unsaturated ring systems, a 6-carboxyhexyl group is best introduced at an earlier stage of the synthesis. Thus, a route to bicyclo [2,2,1] hep-2Z-enes containing a 6-carboxyhexyl group involves an initial Diels-Alder reaction of 8-carboxy-1-formyl-oct-1-ene and cyclopentadiene (a separation of the two trans isomers obtained being required). Introduction of a 3-oxa-6-carboxyhexyl group is similarly best effected at an early stage of the synthesis. A convenient route for doing this involves the use of a compound of structure

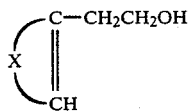

wherein the residue X is a saturated one, such as 6,6-dimethyl-2-(2'-hydroxyethyl)-bicyclo [3,1,1] hept-2-ene, as a starting material. Reaction with acrylonitrile in the presence of Triton B (benzylmethylammonium hydroxide) in a Michael reaction is then used to modify the 2 substituent to form a 5'-cyano-3'-oxapentyl group which is then chain extended using, in turn, lithium aluminium hydride, toluene sulphonyl (Ts) chloride in pyridine, sodium hydride followed by Ts chloride, and cyanide ion to give a 6'-cyano-3'-oxahexyl group by the sequence of reactions

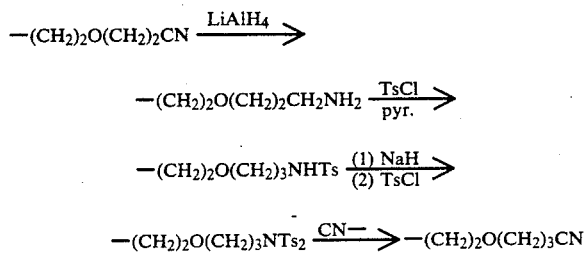

Acid hydrolysis and esterification are then used to convert the cyano group to a methoxycarbonyl group and the reactant 9-borabicyclo [3,3,1] nonane is finally employed to effect reaction at the double bond to yield a compound of the type (II) described hereinbefore having the structure

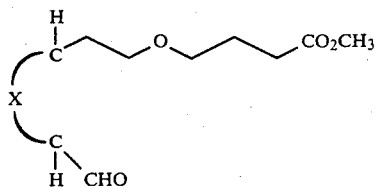

It will be appreciated that the methods described above are not the only ones which may be used for the preparation of compounds according to the present invention and that various alternative procedures may be used as will be apparent to those skilled in the art of prostaglandin chemistry.

It has been found that compounds according to the present invention inhibit the aggregatory activity of 15S-hydroxy-11α-9α-(epoxymethano)-prosta-5Z, 13E-dienoic acid [11, 9-(epoxymethano) $PGH_2$], which is a stable $TXA_2$ mimic, on human platelets and on the rabbit aorta in vitro. Tests on compounds according to the present invention have also illustrated their ability to inhibit the aggregatory activity of both 11, 9-(epoxymethano) $PGH_2$ and collagen in vivo in guinea pigs and of collagen in vivo in rats. Moreover, in the guinea pig tests the Konzett-Rossler test showed inhibition of the bronchoconstrictory effect of both 11, 9-(epoxymethano) $PGH_2$ and the collagen. It is believed that such inhibition is the result of the compounds being thromboxane antagonists and the activity of the compounds is for convenience hereinafter discussed in these terms. Preferred compounds according to the present invention exhibit a pure antagonist activity. However antagonist and agonist activities have been found to be linked in some compounds and in consequence certain of the compounds have been found to show a partial agonist activity in certain tests, such as in the test based on the contractile activity of 11, 9-(epoxymethano) $PGH_2$ on the rabbit aorta strip, although they are antagonists in a platelet test. Such partial agonist activity is most common in the oximes which contain a substituent $C(R^2)=NOR^3$ and it has been found that structural features which tend to endow a compound of this type with a more pure antagonist form of activity are (a) the absence of a halogen substituent, particularly at the para position, in the benzene ring of a phenoxyethyl 0-substituted oxime; (b) the absence of a halogen substituent at the meta position of a benzyl 0-substituted oxime; and (c) the presence of two benzene rings in the oxime substituent, these rings being located, for example, on a carbon atom joined directly to the oxygen atom of the oxime group.

Preferred compounds such as the compounds of Examples 1 and 2 are antagonists in the platelet test, block the aggregatory action of arachidonic acid which is converted to $TXA_2$ by the platelet enzyme system and may or may not block the aggregatory action of ADP which acts via non-$TXA_2$ - sensitive systems. Moreover, they are pure antagonists in the rabbit aorta strip test but do not block the contractile action of noradrenaline which acts on α-adrenoceptors. Some activity has also been observed in compounds according to the present invention on guinea pig tracheal muscle.

Compositions according to the present invention are of interest for the treatment of thrombotic disorders and also for the treatment of anaphylactic disease states, for example as bronchodilators for the treatment of asthma, in hypoxia, etc. They additionally have potential as anti-inflammatory agents. It will be appreciated that the spectrum of activity shown by any particular compound will vary and that certain compounds may be of particular interest in one of these applications whilst other compounds are of particular interest in another of them. Modifications of a compound can have other advantages. Thus, for example, the use of esters and other derivatives of the 6-carboxyhex-2-enyl group or modifications thereof can have advantages in relation to slow release depot preparation through conversion in vivo to the active compound containing a free carboxy group, although the low water solubility of the esters must be taken account of. Alternatively, the use of a compound in which the 6-carboxy group is in salt form, for example the sodium salt, can be of value due to the enhancement of water solubility which generally results.

It will be appreciated that compounds showing a partial enhancing action on thromboxane activity are also of some interest in respect of this activity although to a much lesser extent than with inhibitory activity. Thus, certain compounds according to the present invention may be of interest for laboratory or even for pharmaceutical purposes, for example in the control of bleeding by topical administration which avoids any systemic take-up, by virtue of the thromboxane enhancing facet of their activity which is shown under certain conditions.

The compounds may be formulated for use as pharmaceuticals for both animal and particularly human administration by a variety of methods, but usually together with a physiologically acceptable diluent or carrier. The compounds may, for instance, be applied as an aqueous or oil solution or as an emulsion for parenteral administration, the composition therefore preferably being sterile and pyrogen-free. The preparation of aqueous solutions of compounds in which the group $R^1$ terminates in a free carboxy group may be aided by salt formation. The compounds may also be compounded for oral administration in the presence of conventional solid carrier materials such as starch, lactose, dextrin and magnesium stearate. Alternative formulations are as aerosols, suppositories, cachets, and, for localised treatment, as suitable creams or drops. Without commitment to a rigid definition of dosage, which is difficult in view of the different levels of activity, methods of formulation, and methods of administration, some general guidance may be given. In the case of systemic administration to produce a thromoboxane antagonism the normal daily dosage which is proposed lies in the range from about 0.1 mg to about 10 mg per kilogram (the average weight of a human being about 70 kg) and particularly from about 1 mg to about 5 mg per kilogram. It will be appreciated, however that dosages outside this range may be considered, for example in the case of topical application to produce a localised thromboxane agonism, and that the daily dosage may be divided into two or more portions.

The invention is illustrated by the following Examples.

The compounds of the present invention are related to the compounds described and claimed in our U.K. patent applications of Nos. 8000278 and 8000279 referred to hereinbefore in which bicyclo [2,2,1] heptanes and hept-2Z-enes are disclosed and claimed which are substituted at the 5-position by a 6-carboxyhex-2-enyl group or a modification thereof, and at the 6-position by a group $C(R^2)=NR$ in which $R^3$ represents a group $-OR^3$, $-NH.CO.R^3$ or $-NH.CO.NH-R^3$ and $R^3$ includes the groups $R^3$ described herein. Although such compounds are specifically excluded from the present invention the examples of UKPA Nos. 8000278 and 8000279 further illustrate the wide range of groups of the type $C(R^2)=NR$ which may be present in the compounds of the present invention.

In the Examples, where possible, the stereochemistry which the compounds are believed to possess has been indicated. However, some contamination of a minor nature by other isomers may often be present, i.e. by the other of the pairs of preferred isomers shown hereinbefore or particularly by the corresponding cis isomer. In most cases the compounds are obtained in the form of a racemic mixture but in the case of the compounds of Examples 7, 8 and 9 an optically active starting material is used and these compounds are therefore also optically active. It should also be noted that the full stereochemistry has not been designated in the names of the compounds of Examples 7 & 8 in as far as no attempt has been made to indicate the orientation of the substituents $R^1$ and $C(R^2)=NR$ relative to the two bridging groups $-CH_2-$ and $-C(CH_3)_2-$; the full orientation being as shown in the structure designated $2\alpha$, $3\beta$, $6\alpha$ illustrated hereinbefore.

The mass spectroscopy data given in these examples is obtained by direct inlet except for those cases where the compound has a substituent $R^1$ which terminates in an ester grouping when the data is obtained by gas chromatography mass spectroscopy. In certain cases, which are indicated, the free carboxy group of the substituent $R^1$ is converted to a methyl ester group before the mass spectrum is run (by gas chromatography mass spectroscopy). Such conversion is readily achieved by solution in methanol, using warming and addition of $NaHCO_3$ as necessary, followed by the addition of an excess of ethereal diazomethane to the methanolic solution, standing, and the removal of solvent.

EXAMPLES

EXAMPLE 1

5-endo-(6'-Carboxyhex-2'Z-enyl)-6-exo-[N-(benzylthiocarbamoyl)-hydrazonomethyl]-bicyclo [2,2,1] heptane (1) Maleinaldehydic acid pseudo-ethyl ester 30 g of redistilled furan-2-aldehyde is mixed with 600 ml dry ethanol and 300 mg of methylene blue is added. Dry air is blown gently through the solution and the material is irradiated with a 300 W tungsten lamp for about two days until t.l.c. in a silica gel/ether system shows essentially no remaining starting material. The solution is then stirred with vanadium pentoxide for four hours, filtered, and the solvent removed under reduced pressure. The residual oil is distilled under high vacuum to give the title compound as an oil (23.6 g, 76%), b.p. 90°–92° C./0.2 mm.

(2) Diels-Alder reaction between maleninaldehydic acid pseudo-ethyl ester and cyclopentadiene Freshly cracked cyclopentadiene (9.0 g) is mixed with 11.0 g of the pseudo ester (1). A gentle warming is observed and the mixture is allowed to stand overnight. The n.m.r. spectrum typically shows the formation of the adduct (2) to be complete and the material is taken to the next step without purification.

(3) 5-endo-Ethoxycarbonyl-6-exo-diethoxymethyl-bicyclo [2,2,1] hept-2Z-ene

The Diels-Alder adduct (2) (10 g) is heated in a mixture of triethyl orthoformate (10 ml), dry ethanol (100 ml), and concentrated sulphuric acid (1 ml). The mixture darkens and after 12 hours is cooled and treated with anhydrous potassium carbonate (5 g) and ether (150 ml). Water is then slowly added with efficient mixing to neutralise the acid. The product is extracted with ether, washed with water and distilled to give the title compound as an oil (7.3 g, 63%), b.p. 115°–120° C./0.3 mm.

(4) 5-endo-Ethoxycarbonyl-6-exo-diethoxymethyl-bicyclo [2,2,1] heptane 5-endo-Ethoxycarbonyl-6-exo-diethoxymethyl-bicyclo [2,2,1] hept-2Z (30 g) is dissolved in 200 ml of ethanol and 0.3 g of 10% palladium on charcoal is added. The mixture is vigorously stirred in 1 atmosphere of hydrogen gas at room temperature. 1 molar equivalent of hydrogen gas is absorbed and the product is then isolated by removal of the catalyst by filtration through a Celite pad, followed by evaporation of the filtrate to give a quantitative yield of the title compound as an oil b.p. 105°–110° C./1.5 mm.

(5) 5-endo-Hydroxymethyl-6-exo-diethoxymethyl-bicyclo [2,2,1] heptane

The ester (4) (27 g) is added in ether to a 10% excess of lithium aluminium hydride (2.1 g) in ether with stirring at reflux temperature. The mixture is boiled for 1 hour after the addition and is then quenched by the addition of wet ether followed by 5% aqueous sodium hydroxide to precipitate aluminium salts. The colourless organic phase is dried over magnesium sulphate, filtered and evaporated to give the title compound as an oil (20 g, 91%).

(6) 5-endo-Cyanomethyl-6-exo-diethoxy-bicyclo [2,2,1] heptane

The alcohol (5) (20 g) in a minimum volume of dry pyridine is added slowly to 20 g of p-toluenesulphonyl chloride in 130 ml dry pyridine with stirring at 0° C. The mixture is kept at 5° C. overnight and then poured into a water-ice mixture. The resulting precipitate is filtered off and dried to give the tosylate ester of the alcohol in 85% yield as an off-white solid, m.p. 84°–86° C. (dec.).

The tosylate (14 g) in 15 ml dimethyl sulphoxide is added to 5 g of dry potassium cyanide in 20 ml dimethyl sulphoxide. The mixture is stirred under nitrogen and the temperature slowly raised over 1 hour to 110° C. After 5 hours the reaction mixture is cooled and poured into water. The product is isolated by ether extraction, and purified by distillation to give the title compound (7.8 g, 90%), b.p. 115°–126° C./1.5 mm.

(7) 6-exo-Diethoxymethyl-5-endo-formylmethyl-bicyclo [2,2,1] heptane

The cyano compound (6) (20 g) is stirred at −15° C. in 200 ml dry toluene under nitrogen. Diisobutylaluminium hydride (113 ml of a 1M solution in hexane) is added to the substrate over 25 minutes and the mixture allowed to reach room temperature. After 1 hour, methanol (30 ml) is cautiously added, followed by 400 ml of saturated aqueous sodium hydrogen tartrate. The mixture is stirred and heated at 40° C. for 2 hours. The upper organic layer is separated and the aqueous phase further extracted with ethyl acetate. The combined organic solutions are dried (Mg SO$_4$) and the solvent removed to give a yellow oil. This is chromatographed on Florisil in benzene to give the pure title compound as a colourless oil (17.2 g, 85%), $\nu_{max}$ (film): 1725 cm$^{-1}$.

(8) 5-endo-(6'-Carboxyhex-2'Z-enyl)-6-exo-diethoxymethyl-bicyclo [2,2,1] heptane (4-Carboxy-n-butyl)-triphenylphosphonium bromide (23.3 g) is dried at 75° C. under vacuum for 2.5 hours. The resulting white solid is then cooled, the vacuum released to dry nitrogen, and 30 ml of dimethyl sulphoxide is added. A 2M solution of dimesyl sodium in dimethyl sulphoxide (50 ml) is added slowly while the mixture is maintained at 25° C. with a water bath. After 15 minutes the aldehyde (7) (5.0 g) is added to the deep red ylide thus produced. The mixture is stirred overnight and then the solvent is removed at 55°–60° C. under vacuum. The residue is dissolved in water, and the aqueous phase is extracted with ether and then carefully acidified to pH4 with 2N HCl. The precipitate is extracted into ether and the ethereal solution is dried and concentrated to give the title compound as an oil (3.7 g, 55%).

(9) 5-endo-(6'-Carboxyhex-2'Z-enyl)-6-exo-formyl-bicyclo [2,2,1] heptane

The acid/acetal (8) (1.8 g) is dissolved in 200 ml chloroform and 50 ml of concentrated hydrochloric acid is added to form a two phase system. The mixture is vigorously stirred for 90 minutes and is then extracted with ether and the ethereal solution dried and concentrated. The residual oil is purified by silicic acid chromatography, the oil being applied to the column (prepared by slurrying 10 g of Unisil silicic acid - Clarkson Chemical Co., USA - in hexane and pouring into a glass chromatography column) in hexane and elution being carried out with increasing proportions of diethyl ether in hexane up to pure diethyl ether. The chromatography gives the title compound as a colourless oil (1.4 g, 83%), $\delta$(CDCl$_3$) 1.2 to 2.6 (18H,m), 5.4 (2H,m), 9.6 (1H,d). Note: Care should be taken to avoid contact of this compound with methanol since it very readily forms a dimethyl acetal.

(10) 5-endo(6'-carboxyhex-2'Z-enyl)-6-exo-[N-(benzylthiocarbamoyl)hydrazonomethyl]-bicyclo [2,2,1] heptane The aldehyde/acid (9) (100 mg) is heated at 60° C. with benzylthiosemicarbazide (110 mg) in tetrahydrofuran (THF) (5 ml) for 2 hours. The THF is removed in vacuo, and the resulting product is purified by silica gel chromatography (10 g charge), eluting with a linear gradient from 10% v/v ethyl acetate in benzene to pure ethyl acetate and monitoring the fractions by t.l.c. The chromatography gives the title compound as a yellow oil (85 mg), $\lambda_{max}$ (CH$_3$OH) 270 nm, $\epsilon_{max}$ 25,200, $\delta$(CDCl$_3$) 4.90 (d,2H), 5.30 (m, 2H), 7.20 (d), 7.35 (s, 5H), 7.60 (t, 1H), 10.2 (br, 2H); M+ 413 (very small, M-2 prominent).

The benzylthiosemicarbazide is prepared as follows.

Dicyclohexylcarbodiimide (10.3 g) and carbon disulphide (20 ml) are stirred in a round-bottomed flask with 20 ml of diethyl ether at −10° C. Benzylamine (5.35 g, 5.5 ml) in 20 ml ether is added slowly when a white precipitate forms immediately. The reaction mixture is stirred overnight, filtered and the ether removed in vacuo. The residue is suspended in ether, filtered and the ether removed in vacuo. The remaining oil is distilled under vacuum (0.5 mm, 100° C. approx.) to give benzylisothiocyanate as an oil (4.7 g, 62%).

Benzylisothiocyanate (4.0 g) is slowly added to 1.8 g of anhydrous hydrazine in 50 ml dioxane. The reaction mixture is stirred at room temperature, the dioxane is then removed in vacuo and the residue is recrystallised from ethanol to give 4-benzylthiosemicarbazide as a crystalline solid (2.5 g), m.p. 127.6° C.

EXAMPLE 2

5-endo(6'-Carboxyhex-2'Z-enyl)-6-exo-{1'-[N-(phenylthiocarbamoyl)-hydrazono]-ethyl}-bicyclo [2,2,1] heptane (1) 5-endo-(6'-Carboxyhex-2'Z-enyl)-6-exo-(1'-hydroxyethyl)-bicyclo [2,2,1] heptane 5-endo-(6'-Carboxyhex-2'Z-enyl)-6-exo-formyl-bicyclo [2,2,1] heptane is prepared as described in Example 1(9). This aldehyde/acid (250 mg) is dissolved in dry tetrahydrofuran (10 ml) at 0° C. and treated under nitrogen and with stirring over 30 minutes with a 1M solution of methyl magnesium iodide in ether (2 ml). The mixture is stirred under nitrogen overnight whilst it is allowed to come to room temperature. The reaction is then quenched by the addition of dilute aqueous hydrochloric acid and the product is extracted with ether (3×), the ether solution is dried and evaporated to give the title compound as an oil (200 mg). A small sample is treated to form the methyl ester trimethylsilyl ether and on gas chromatography mass spectroscopy on a 3% OVI column this shows a carbon value of 18.2, a $M^+$ value of 352 and a base peak of 117.

Chromatography on a column of Sephadex LH 20 substituted with Nedox 1114 olefin oxide to 20% w/w (Lipidex) of the bulk of the oily product using a mixture of (all proportions by volume) 100 parts of hexane, 100 parts of 1,2-dichloroethane, 5 parts of ethanol and 0.1% of the total of glacial acetic acid, as eluant yields the two isomeric secondary alcohols differing in the configuration at the newly introduced asymmetric carbon atom (—CHOH.CH$_3$). N.m.r spectroscopy on these isomeric products in CDCl$_3$ gives the following δ values: First isomer eluted: 7.3 (s, broad, 1H), 5.45 (m, 2H), 3.6 (m-qxd, 1H), 2.5–1.0 (m, 21H), 1.2 (d). Second isomer eluted: 7.8 (s, broad, 1H), 5.4 (m, 2H), 3.55 (m-qxd), 2.5–1.0 (m, 18H), 1.2 (d).

(2) 5-endo-(6'-Carboxyhex-2'Z-enyl)-6-exo-acetyl-bicyclo [2,2,1] heptane

The procedure described under (1) is repeated with 600 mg of the aldehyde to give a mixture of the two isomeric alcohols (500 mg). This mixture is dissolved in pure acetone (15 ml) and the solution is cooled to 0° C. Jones reagent (600 μl of a solution prepared by dissolving 26.7 g of chromic anhydride in 23 ml of concentrated sulphuric acid and diluting to 100 ml with water, followed by filtration) is added slowly to the cooled solution with vigorous stirring over 15 minutes. After a further 10 minutes stirring at 0° C. the mixture is poured into water and the product extracted with ether. The ether solution is dried and evaporated to give the title compound as an oil (about 75% overall yield from formyl compound), δ(CDCl$_3$) 10.0 (s-broad, 1H), 5.4 (m, 2H), 2.8–1.1 (m, 21H), 2.2 (s). G.C.M.S. (3% OVI) on the methyl ester gives a carbon value of 17.15, a $M^+$ value of 278 and a base peak of 43/137.

(3) 5-endo-(6'-Carboxyhex-2'Z-enyl)-6-exo-{1'-[N-(phenylthiocarbamoyl)-hydrazono]-ethyl}-bicyclo [2,2,1] heptane The ketone (2) (100 mg) is heated at 60° C. with phenylthiosemicarbazide (110 mg; prepared by an analogous procedure to that described for 4-benzylthiosemicarbazide in Example 1 (10) and having m.p. 113.7° C.) in dioxane (5 ml) for 2 hours. The dioxane is removed in vacuo, and the resulting product is purified by silica gel chromatography (10 g charge), eluting with a linear gradient from 10% v/v ethyl acetate in benzene to pure ethyl acetate and monitoring the fractions by t.l.c. The chromatography gives the title compound as an oil (107 mg), $\lambda_{max}$ (CH$_3$OH) 277 nm, $\epsilon_{max}$24, 780, δ(CDCl$_3$) 2.00 (s, 3H), 5.35 (m,2H), 7.2–7.7 (m, 5H), 8.95 (br, 1H), 9.30 (br, 1H), $M^+$ 413 (very small, M-2 prominent).

EXAMPLE 3

5-endo-(6'-Carboxyhex-2'Z-enyl)-6-exo-{1'-[N-(phenylthiocarbamoyl)-hydrazono]-propyl}-bicyclo [2,2,1] heptane (1) 5-endo-(6'-Carboxyhex-2'Z-enyl)-6-exo-(1'-hydroxypropyl)bicyclo [2,2,1] heptane 5-endo-(6'-Carboxyhex-2'Z-enyl)-6-exo-formyl-bicyclo [2,2,1] heptane is prepared as described in Example 1(9). This acid/aldehyde (600 mg) is dissolved in dry tetrahydrofuran (25 ml) at 0° C. and treated under nitrogen and with stirring over 30 minutes with a 0.5M solution of ethyl magnesium bromide in ether (10 ml). The solution is allowed to warm up to room temperature and is then treated with dilute aqueous hydrochloric acid and the product extracted with ether (3×). The ethereal extracts are dried and evaporated to give the title compound as an oil. A small sample is treated to form the methyl ester trimethylsilyl ether and on gas chromatography mass spectroscopy this shows prominent ions at m/e values of 366 ($M^+$), 337 (M-29), 276 (M-90) and 131 (C$_2$H$_5$.CH.OTMS).

The bulk of the oil is subjected to gel partition chromatography on a column of Sephadex LH20 substituted with Nedox 1114 olefin oxide to 20% w/w (Lipidex) using as eluant a mixture of (all proportions by volume) 100 parts hexane, 100 parts 1,2-dichloroethane, 5 parts ethanol and 0.1% of the total of glacial acetic acid. The chromatography separates the product into two main zones corresponding to the two isomeric secondary alcohols differing in configuration at the newly introduced asymmetric carbon atom (—CHOH.CH$_3$). N.m.r. spectroscopy on these isomeric products in CDCl$_3$ gives the following δ values. First isomer eluted: 7.5 (broad, 2H), 5.4 (m, 2H), 3.22 (d x t, 1H), 2.5–0.9 (m, 25H). Second isomer eluted: 7.5 (br, 2H), 5.4 (m, 2H), 3.40 (m, 1H), 2.5–1.0 (m, 25H).

(2) 5-endo-(6'-Carboxyhex-2'Z-enyl)-6-exo-propionyl-bicyclo [2,2,1] heptane

The alcohol/acid (1) of the first zone (145 mg) is oxidized with Jones reagent at 0° C. in acetone in an exactly analogous manner to that described in Example 2(2) to give the title compound as an oil (95 mg), δ(CDCl$_3$) 9.0 (br, 1H), 5.35 (m, 2H), 2.7–0.9 (m, 23H), $M^+$ 292 together with 235 (M-57) and 151 (M-141) (as methyl ester - a single peak being obtained on gas chromatography).

The alcohol/acid (1) of the second zone is treated similarly to give the same product (105 mg).

(3) 5-endo-(6'-Carboxyhex-2'Z-enyl)-6-exo-{1'-[N-(phenylthiocarbamoyl)-hydrazono]-propyl}-bicyclo [2,2,1] heptane The ketone/acid (2) (100 mg) and phenylthiosemicarbazide (110 mg) in dioxane (5 ml) are heated to 50° C. overnight. The dioxane is removed in vacuo, and the resulting product is purified by silica gel chromatography (10 g charge) eluting with a linear gradient from 10% v/v ethyl acetate in benzene to pure ethyl acetate and monitoring the fractions by t.l.c. The chromatography gives the title compound as an oil (20 mg, 15%), $\lambda_{max}$(CH$_3$OH) 277 nm, $\epsilon_{max}$ 22,380, $\delta$(CDCl$_3$) 9.7 (br, 1H), 9.1 (br, 1H), 7.8–7.0 (m, 5H), 5.4 (m, 2H), 2.5–1.0 (m, 23H), M+ 427.

EXAMPLE 4 trans-5-(6'-Carboxyhex-2'Z-enyl)-6-[N-(phenylcarbamoyl)-hydrazonomethyl]-bicyclo [2,2,2] octane (1) Diels-Alder reaction between maleinaldehydic acid pseudo-ethyl ester and cyclohexadiene Cyclohexadiene (4.5 g) and the maleinaldehyde acid pseudo-ethyl ester described in Example 1(1) (6.4 g) are heated together in a thick walled glass tube at 120° C. for 10 hours and the product is distilled to give the Diels-Alder adduct of these two compounds in over 90% yield, b.p. 95°–97° C./0.2 mm, M+ 208.

(2) 5-endo-Hydroxymethyl-6-exo-(1',3'-dioxacyclopent-2'-yl)-bicyclo [2,2,2] oct-2Z-ene The Diels-Alder adduct (1) (10 g) is heated under a Dean and Stark apparatus with 12 ml of ethylene glycol in 100 ml toluene containing a crystal of p-toluenesulphonic acid. After water has ceased to form, half of the solvent is distilled off and the resultant solution of 5-endo-ethoxycarbonyl-6-exo-(1',3'-dioxacyclopent-2'-yl)-bicyclo [2,2,2] oct-2Z-ene is added to excess lithium aluminium hydride (3 g) in 200 ml of dry ether. The addition is performed at a rate which maintains a gentle boiling of the ether (30 to 60 minutes). After a further 1 hour of heating the excess hydride is destroyed by the careful addition of wet ether followed by water. The mixture is then treated with aqueous 10% w/v sodium hydroxide solution to precipitate aluminium salts. The mixture is dried over magnesium sulphate and then filtered. The organic solvent is evaporated to give the title compound as an oil which is used directly in step (3).

(3) trans-5-Hydroxymethyl-6-(1',3'-dioxacyclopent-2'-yl)-bicyclo [2,2,2] octane

The crude alcohol/acetal obtained in (2) is dissolved in ethanol and hydrogenated at atmospheric pressure over 10% palladium on charcoal, one molecular equivalent of hydrogen being absorbed. The catalyst is filtered off and the solvent evaporated. Distillation of the residue gives the title compound as a colourless oil (6.1 g, 60%), b.p. 110°–112° C./0.15 mm.

(4) trans-5-Cyano-6-(1',3'-dioxacyclopent-2'-yl)-bicyclo [2,2,2] octane

The alcohol/acetal (3) (7.0 g) in 15 ml dry pyridine is added to 7.5 g of p-toluenesulphonyl chloride in 45 ml of pyridine at 0° C. with stirring. After 20 hours the mixture is poured into ice/water and after 30 minutes stirring the mixture is extracted with ether to give the tosylate ester of the alcohol as a colourless oil in good yield.

The tosylate ester (12.0 g) in dimethyl sulphoxide (15 ml) is added to potassium cyanide (3.0 g) in dimethyl sulphoxide (20 ml). The mixture is stirred and heated at 100° C. under nitrogen for 6 hours. The reaction mixture is then poured into water and the mixture is extracted with ether to give the title compound as an oil (7.2 g), $\nu_{max}$2205 cm$^{-1}$ which is purified by passage through a short Florisil column with toluene as eluant.

(5) trans-5-Formylmethyl-6-(1',3'-dioxacyclopent-2'-yl)-bicyclo [2,2,2] octane

The nitrile/acetal (4) (7.0 g) is stirred in 100 ml of dry toluene under nitrogen at −15° C. Di-isobutylaluminium hydride, (42.5 ml of 1M solution in toluene) is added slowly over 25 minutes and the mixture is allowed to warm slowly to room temperature. After 1 hour, methanol (10 ml) is slowly added, followed by 200 ml of saturated aqueous sodium hydrogen tartrate. The mixture is stirred at 40° C. for 2 hours and the upper organic layer is then separated and the aqueous phase further extracted with ethyl acetate. The combined organic solutions are dried (MgSO$_4$) and evaporated. The yellow oil obtained is chromatographed on Florisil in toluene to give the title compound as an oil (5.8 g, 83%), $\nu_{max}$ (film) 1720 cm$^{-1}$, $\delta$(CDCl$_3$) 9.75 (t, J=2 Hz, 1H), 4.85 (d, J=8 Hz, 1H), 3.9 (m, 4H), 2.8–2.4 (m, 2H), 2.1–1.2 (m, 12H).

(6) trans-5-(6'-Carboxyhex-2'Z-enyl)-6-formyl-bicyclo [2.2.2] octane

4-Carboxy-n-butyltriphenylphosphonium bromide (17.0 g) is dried at 75° C. for 3 hours under vacuum. The solid is cooled and the vacuum released to argon. Dimethyl sulphoxide (50 ml) is added and butyllithium (270 ml of a 1.5M solution in pentane) is added slowly over 1 hour. The deep red ylide thus formed is stirred at room temperature for 15 minutes and then the aldehyde/acetal (5) (4.6 g) is added slowly over 15 minutes. The mixture is stirred overnight at room temperature, and then the solvent is removed at 50°–60° C. under vacuum. The residue is dissolved in water and the aqueous phase is extracted with ether to remove non-acidic material. The water layer is acidified (pH=4) with 2N aqueous hydrochloric acid and then extracted with ether. The ethereal solution is dried and evaporated to give trans-5-(6'-carboxyhex-2'Z-enyl)-6-(1',3'-dioxacyclopent-2'-yl)-bicyclo [2,2,2] octane as an oil (3.5 g, 55%).

The acetal group is removed by stirring this material (3 g) with 200 ml of water/dioxane (1:1 v/v) containing 0.1N aqueous hydrochloric acid at 40° C. The mixture is extracted with ether and the ethereal extract is dried (MgSO$_4$) and evaporated to give a residue which is purified by chromatography on silica gel in toluene/ethyl acetate (90:10 v/v) to give the title compound as an oil [2.3 g, 48% from (5)], $\nu_{max}$ (film) 1725 and 1710 cm$^{-1}$, $\delta$(CDCl$_3$) 9.73 (s, 1H), 5.5–5.3 (m, 2H), and 2.2–1.45 (m, 20H).

(7) trans-5-(6'-Carboxyhex-2'Z-enyl)-6-[N-(phenylcarbamoyl)hydrazonomethyl]-bicyclo [2,2,2] octane The acid/aldehyde (6) (100 mg) is heated with phenyl semicarbazide (85 mg) in dioxane for 2 hours at 40° C. The solvent is then evaporated and the residue purified by liquid-gel partition chromatography using a 400×15 mm column of Sephadex LH20 substituted with Nedox 1114 olefin oxide to 20% w/w and eluting with dichloroethane/hexane/ethanol (100:100:5 v/v/v) containing 0.1% v/v of acetic acid. The chromatography gives the title compound as an oil (87 mg), $\delta$(CDCl$_3$) 9.60 (br, 1H), 8.10 (br, 1H) 7.7–7.1 (m, 5H), 5.35 (m, 2H).

The phenyl semicarbazide is prepared as follows. Ethyl-N-phenyl carbamate (8.25 g) is refluxed with hydrazine hydrate (3.75 g) for 3 hours. The mixture is evaporated to dryness and the residue is treated with ether, and the solid phenyl semicarbazide (1.5 g) is filtered off, washed with ether and dessicated, m.p. 122°-124° C. Note: In a variant of the procedure described in this Example the acid/aldehyde (6) (100 mg) is reacted with p-fluorobenzoic hydrazide

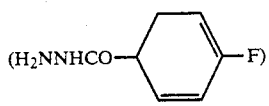

(45 mg) in place of the phenyl semicarbazide

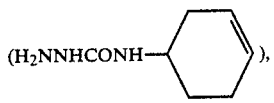

the reaction being carried out in tetrahydrofuran for 1.5 hours at 40° C. to yield the alternative bicyclo [2,2,2] octane derivative, trans-5-(6'-carboxyhex-2'Z-enyl)-6-[N-(p-fluorobenzoyl)-hydrazono methyl]-bicyclo [2,2,2] octane.

The p-fluorobenzoic acid hydrazide is prepared as follows. Ethyl p-fluorobenzoate (8.4 g) is refluxed with hydrazine hydrate (3.75 g) for 3 hours. The mixture is then cooled, ether is added and the precipitate of p-fluorobenzoic acid hydrazide (3.2 g) is removed by filtration, washed with ether and desiccated, m.p. 149°-151° C.

EXAMPLE 5 trans-5(6'-Carboxyhex-2'Z-enyl)-6-{1'-[N-(phenylthiocarbamoyl)-hydrazono]-ethyl}-bicyclo [2,2,2] octane (1) trans-5-(6'-Carboxyhex-2'Z-enyl)-6-acetyl-bicyclo [2,2,2] octane trans-5-(6'-Carboxyhex-2'Z-enyl)-6-formyl-bicyclo [2,2,2] octane is prepared as described in Example 4. This acid/aldehyde (2 g) is dissolved in dry tetrahydrofuran (20 ml) at 0° C. and treated under nitrogen with 1M solution of methyl magnesium bromide in ether (23 ml) during 2 hours. The reaction is quenched by the addition of dilute aqueous hydrochloric acid and the mixture is extracted with ether (3×). The ethereal solution is dried and evaporated to give a residue which is chomatographed on silica gel using increasing proportions of ethyl acetate in toluene as eluant. Traces of the starting material are eluted with 20% v/v ethyl acetate in toluene and 50% v/v ethyl acetate in toluene elutes trans-5-(6'-carboxyhex-2'Z-enyl-)-(1'-hydroxyethyl)-bicyclo [2,2,2] octane in the form of an epimeric mixture differing in configuration at the asymmetric carbon atom of the group —CHOHCH₃.

The solution of the epimeric alcohols is evaporated and the residue (1.6 g) in acetone (20 ml) is oxidized using Jones reagent [2.2 ml, prepared as described in Example 2(2)] at 0° C. for 30 minutes. The reaction mixture is worked up as described in Example 2(2) to give trans-5-(6'-carboxyhex-2'Z-enyl)-6-acetyl bicyclo [2,2,2] octane as an oil (1.3 g), $\delta(CDCl_3)$ 5.4 (m, 2H), 2.2 (s, 3H) 2.6-1.3 (m, 20H), M+ 291 and also 249 (M-43) and 151 (M-141) (as methyl ester).

(2) trans-5-(6'-Carboxyhex-2'Z-enyl)-6-{1'-[N-(phenylthiocarbamoyl)-hydrazono]-ethyl}-bicyclo [2,2,2] octane The acid/ketone (1) (30 mg is heated at 40° C. with phenylthiosemicarbazide [115 mg, prepared as described in Example 2(3)] in dioxane for 2 hours. The solvent is removed in vacuo and the residue is purified by gel partition chromatography on a column of Sephadex LH20 substituted with Nedox 1114 olefin oxide to 20% w/w (Lipidex) using as eluant a mixture of (all proportions by volume) 100 parts of hexane, 100 parts of 1,2-dichloroethane, 5 parts of ethanol and 0.1% of the total of glacial acetic acid. The chromatography gives the title compound as an oil (17 mg), $\delta(CDCl_3)$ 9.50 (br, 1H), 8.75 (br, 1H), 7.7-7.1 (m, 5H), 5.35 (m, 2H), 2.0 (s) and 2.18 (s, 3H together - may be due to syn/anti isomerism).

EXAMPLE 6

5-exo-(6'-Carboxyhex-2'Z-enyl)-6-endo-[N-(phenylthiocarbamoyl)-hydrazonomethyl]-7-oxa-bicyclo [2,2,1] heptane (1) Diels-Alder reaction between furan and maleic anhydride Furan and maleic anhydride are reacted at room temperature in benzene, crystallisation of the adduct occurring from the reaction mixture.

(2) 6-exo-Carboxy-5-exo-hydroxymethyl-7-oxa-bicyclo [2,2,1] heptane lactone

Sodium borohydride (0.75 g) in dimethylformamide is stirred at 0° C. and the Diels-Alder adduct (2.5 g) is added in dimethylformamide. After stirring for 3 hours the solvent is removed by evaporation under vacuum and the residue is treated with an excess of 1M aqueous sulphuric acid. The mixture is extracted repeatedly with chloroform and the combined chloroform extracts are then dried (MgSO₄) and evaporated to give the title compound as a solid (1.5 g, 65%), m.p. 123°-124° C.

(3) 6-exo-formyl-5-exo-hydroxymethyl-7-oxa-bicyclo [2,2,1] heptane lactol

The lactone (2) (4.6 g), in dry toluene (70 ml) is treated with stirring at 0° C. with 24 ml of a 25% w/v solution of diisobutylaluminium hydride in toluene. The lactone slowly dissolves and after a further 2 hours at room temperature the reaction is quenched by the addition of methanol (6 ml) followed by treatment with a saturated aqueous solution of sodium hydrogen tartrate (95 ml). The mixture is stirred at 40° C. for 2 hours and the organic phase is then separated. Evaporation of the organic phase gives some product and a further amount is obtained by evaporation of the aqueous phase under vacuum, leaching of the residue with chloroform and evaporation of the dried chloroform extracts. Combination of the two products gives the title compound [in which the >C=O group of the lactone (2) is converted to a >CHOH group] as a solid (1.5 g, 60%), m.p. 123°-124° C., $\delta(CDCl_3)$ 5.3 (m, 1H), 4.50 (m, 1H), 4.35 (m, 1H), 4.1 (d x d, 1H), 3.75 (d x d, 1H), 3.65 (c, 1H), 2.4 (m, 2H), 1.5 (m, 4H).

(4) 5-exo-Hydroxymethyl-6-endo-(1',3'-dioxacyclopent-2-yl)-7-oxa-bicyclo [2,2,1] heptane The lactol (3) (1.0 g) is treated with ethylene glycol (1.0 g) in benzene (50 ml) and a catalytic amount (a crystal) of toluene sulphonic acid is added. The mixture is heated under a Dean and Stark head for 20 hours and the solvent is then evaporated under vacuum to give the title compound (in which conversion of the 5-substituent to the endo configuration appears to have occurred), $\delta(CDCl_3)$ 5.0 (s, 1H), 4.5 (m, 2H), 4.0 (m, 2H), 3.7 (s-broad, 4H), 3.2 (s-broad, 1H), 2.5 (m, 2H), 1.6 (m, 4H).

This compound (4) corresponds to the similar intermediate compound in the synthetic route to the bicyclo

[2,2,2] octane compounds which is described in Example 4(2) but with the stereochemistry being different. The compound (4) is converted to 5-exo-(6'-carboxyhex-2'Z-enyl)-6-endo-formyl-7-oxa-bicyclo [2,2,1] heptane which through reaction with phenylthiosemicarbazide, in an analogous fashion to that used for a similar reaction in Examples 2 and 5 etc., is converted to 5-exo-(6'-carboxyhex-2'Z-enyl)-6-endo[N-(phenylthiocarbamoyl)-hydrazonomethyl]-7-oxa-bicyclo [2,2,1] heptane. In working up the various compounds it should be borne in mind that the 7-oxa-bicyclo [2,2,1] heptane series of compounds show a greater water solubility than their bicyclo [2,2,1] heptane and bicyclo [2,2,2] octane counterparts.

EXAMPLE 7

2-α-(6'-Carboxyhex-2'Z-enyl)-3-β-[N-(phenylthiocarbamoyl)-hydrazonomethyl]-6,6-dimethyl-bicyclo [3,1,1] heptane (1) 2-(2'-Benzyloxyethyl)-6,6-dimethyl-bicyclo [3,3,1]-hept-2-ene 2-(2'-Hydroxyethyl)-6,6-dimethyl-bicyclo [3,3,1] hept-2-ene [(−)-nopol] (66 g) is added slowly with stirring to 12.5 g of 80% sodium hydride dispersion in oil in 300 ml of dimethylformamide at room temperature. After addition (ca. 1 hour), stirring is continued for 4–5 hours until all hydrogen evolution has ceased. Benzyl chloride (52 g, 46 ml) is added over 1–2 hours at room temperature when an exothermic reaction is observed. After the addition, the mixture is heated at 80° C. for 4 hours. The material is then cooled, poured into water and the product isolated by ether extraction followed by distillation under vacuum to give the title compound as an oil (71 g, 70%), b.p. 128°–131° C./0.2 mm.

(2) 2-α-(2'-Benzyloxyethyl)-3-β-formyl-6,6-dimethyl-bicyclo [3,1,1] heptane

The benzyl ether (1) (10.2 g) is placed in a large flask (1 l.) with 30 ml THF (dry) under argon and 9-borabicyclo [3,3,1] nonane (9-BBN) in THF (90 ml of 0.5M solution) is added over 5–10 minutes at room temperature. The solution is refluxed for 30 hours maintaining the inert atmosphere, after which most of the compound has reacted at the double bond.

The hydroborated benzyl ether is cooled to 0° C. while the argon atmosphere is replaced by carbon monoxide. A solution of lithium trimethoxyaluminium hydride (62 ml of 0.7M) is prepared from lithium aluminium hydride and methanol in THF and added over 30–60 minutes with vigorous stirring maintaining a positive pressure of carbon monoxide in the system. A vigorous uptake of gas is observed (ca. 1,000 ml) and after a further 1 hour of vigorous stirring the argon atmosphere is re-established and 82 ml of pH7 aqueous saturated phosphate buffer (buffer prepared from 97.5 g $NaH_2PO_4.2H_2O + 108.75$ g $K_2HPO_4$ dissolved in 250 ml water) is added with vigorous stirring. Finally 15 ml of 30% hydrogen peroxide is carefully added while keeping the temperature of the mixture below 20° C. The mixture is stirred for a further 10 minutes and then poured into water. The title compound is isolated by ether extraction and purified by chromatography on Florisil eluting with petrol/ether, being obtained as an oil (8.9 g, 81%), $v_{max}$ (film) 1718 $cm^{-1}$.

(3) 2-α-(2'-Benzyloxyethyl)-3-β-(dimethoxymethyl)-6,6-dimethyl-bicyclo [3,1,1] heptane The benzyl ether/aldehyde (2) (10 g) is dissolved in 100 ml of methanol containing 10 ml trimethyl orthoformate. A few crystals of p-toluene sulphonic acid are added and the mixture is kept overnight. The solution is treated with anhydrous sodium carbonate (0.5 g) and water (20 ml) is slowly added with efficient mixing. The mixture is added to excess water and the title compound isolated by ether extraction in impure form as an oil in 100% yield, $M^+$ 342.

(4) 2-α-(2'-Hydroxyethyl)-3-β-(dimethoxymethyl)-6,6-dimethyl-bicyclo [3,1,1] heptane The benzyl ether/acetal (3) (10 g) is dissolved in 100 ml of methanol and 300 mg of 10% palladium on charcoal* is added. The mixture is then hydrogenated at room temperature and atomspheric pressure. After take up of 1 molar equivalent of hydrogen the title compound is isolated in impure form as an oil in 100% yield by filtration of the mixture through Celite and evaporation of the methanol.

*Some samples of catalyst may be found to encourage cyclisation of the debenzylated compound to give a cyclic acetal. In the event of this presenting difficulty, an alternative procedure is to use sodium in liquid ammonia for this stage.

(5) 2-α-(2'-Formylmethyl)-3-β-(dimethoxymethyl)-6,6-dimethyl-bicyclo [3,1,1] heptane The alcohol/acetal (4) (5.0 g) is dissolved in dry methylene chloride (10 ml) and the solution is added with stirring over 10 minutes to pyridinium chlorochromate (6.0 g) in 30 ml methylene chloride containing 0.5 g of dry finely divided sodium acetate. After 2 hours, 200 ml of dry ether is added to the mixture and after a further 15 minutes, the mixture is poured into water. The ether layer is quickly washed with 3% aqueous sodium hydroxide (2×200 ml), followed by brine. The solution is dried over sodium sulphate, the ether evaporated and the residue chromatographed on Florisil with benzene/ether as eluant to give the title compound (2.1 g, 43%), $v_{max}$(film) 1720 $cm^{-1}$, $M^+$ 240.

(6) 2-α-(6'-Carboxyhex-2'Z-enyl)-3-β-(dimethoxymethyl)-6,6-dimethyl-bicyclo [3,1,1] heptane The aldehyde/acetal (5) (0.5 g) is reacted with 2.2 equivalents of 4-carboxy-n-butyl-triphenyl-phosphonium bromide in the presence of dimesyl sodium in dimethyl sulphoxide as described for the bicyclo [2,2,1] acid/acetal in Example 1(8) to give the title compound in a high purity (0.51 g, 72%), $M^+$ 338.

(7) 2-α-(6'-Carboxyhex-2'Z-enyl)-3-β-formyl-6,6-dimethyl-bicyclo [3,1,1] heptane The acid/acetal (6) (0.5 g) is dissolved in 20 ml of dioxane-water mixture (1:1) and the solution is heated at 40° C. for 2.5 hours with an excess of 0.2M aqueous hydrochloric acid. The title compound is isolated as an oil by extraction with ether followed by chromatography on silicic acid eluting with 5% ether in toluene (0.36 g, 72%), $v_{max}$(film) 1720 $cm^{-1}$, $\delta(CDCl_3)$ 0.7 (d, 1H), 1.2 (s, 3H), 1.5–2.8 (m, 15H), 5.4 (m, 2H), 8.5 (s, very broad, 1H), 9.6 (d, 1H), $M^+$ 292 (methyl ester).

(8) 2-α-(6'-Carboxyhex-2'Z-enyl)-3-β-[N-(phenylthiocarbamoyl)hydrazonomethyl]-6,6-dimethyl-bicyclo [3,1,1] heptane The acid/aldehyde (7) (100 mg) is heated with 4-phenylthiosemicarbazide (100 mg) in 5 ml dioxane at 60° C. for 2 hours. The solvent is removed in vacuo and the residue purified on Lipidex using the procedure described in Example 2(1) to give the title compound as an oil (126 mg), $\lambda_{max}(CH_3OH)$ 274.5 nm, $\epsilon_{max}$ 16,650, $\delta(CDCl_3)$ 1.10 (s, 3H), 1.25 (s, 3H), 5.40 (m, 2H), 7.2–7.7 (m, 5H), 9.05 (br, 1H), 10.30 (br, 1H), $M^+$ 427 (very small, M-2 prominent).

EXAMPLE 8

2-α-(6'-Carboxyhex-2'Z-enyl)-3-β-{1'-[N-(phenylcarbamoyl)-hydrazono]-ethyl}-6,6-dimethyl-bicyclo [3,1,1] heptane (1) 2-α-(6'-Carboxyhex-2'Z-enyl)-3-β-acetyl-6,6-dimethyl-bicyclo [3,1,1] heptane 2-α-(6'-Carboxyhex-2'Z-enyl)-3-β-formyl-6,6-dimethyl-bicyclo [3,1,1] heptane is prepared as described in Example 7(7). This acid/aldehyde (1.1 g) is dissolved in dry tetrahydrofuran (20 ml) and treated at 0° C. under nitrogen with a 1M solution of methyl magnesium bromide in diethyl ether (12 ml). The mixture is stirred overnight and is then allowed to come to room temperature and is quenched by the addition of dilute aqueous hydrochloric acid. The mixture is extracted with ether (3×) and the ether solution is dried and evaporated to give, as an oil, 2-α-(6'-carboxyhex-2'Z-enyl)-3-β-(1'-hydroxyethyl)-6,6-dimethyl-bicyclo [3,1,1] heptane in the form of an epimeric mixture differing in configuration at the asymmetric carbon atom of the group —CHOHCH$_3$.

The acid/alcohol mixture is treated with Jones reagent (1.25 ml) in acetone at 0° C. for 30 minutes in an analogous fashion to that described in Example 2(2). The reaction mixture is then quenched with water and the product immediately extracted with ether. The ether solution is dried and evaporated and the oily residue is chromatographed on silica gel using increasing concentrations of ethyl acetate in toluene as eluant. The bulk of the desired product is contained in the 20% v/v ethyl acetate/toluene fraction which is evaporated to give the title compound (0.625 g), δ(CDCl$_3$) 5.35 (m, 2H), 2.18 (s, 3H), 3.0–1.6 (m, 17H), 1.07 (s, 3H), 1.22 (s, 3H), 0.87 (d, 1H), M+ 306 and also 263 (M-43), 165 (M-141) and 125 (on methyl ester). The methyl ester-butyl oxime derivative, unlike the methyl ester, shows twin peaks on gas chromatography (syn/anti isomers). The major compound on g.c.m.s. shows prominent ions at m/e 377 (M+), 320 (M-57), 304 (M-73), 142 and 116.

(2) 2-α-(6'-Carboxyhex-2'Z-enyl)-3-β-{1'-[N-(phenylcarbamoyl)hydrazono]-ethyl}-6,6-dimethyl-bicyclo [3,1,1] heptane The acid/ketone (1) (100 mg) is heated at 40° C. with phenylsemicarbazide [90 mg, prepared as described in Example 4 (7)] in dioxane for 2 hours. The solvent is removed in vacuo and the residue is purified by gel partition chromatography on a column of Sephadex LH20 substituted with Nedox 1114 olefin oxide to 20% w/w (Lipidex) using as an eluant a mixture of (all proportions by volume) 100 parts of hexane, 100 parts of 1,2-dichloroethane, 5 parts of ethanol and 0.1% of the total of glacial acetic acid. The chromatography gives the title compound as an oil (75 mg), δ(CDCl$_3$), 9.20 (br, 1H), 8.30 (br, 1H) 5.40 (m, 2H) 1.98 (s, 3H), 1.24 (s, 3H), 1.12 (s, 3H).

EXAMPLE 9

3-β-(6'-Carboxyhex-2'Z-enyl)-2-[N-(phenylcarbamoyl)-hydrazonomethyl]-6,6-dimethyl-bicyclo [3,1,1] heptane (1) 2-(Vinyloxymethyl)-6,6-dimethyl-bicyclo [3,1,1] hept-2-ene A mixture of 2-hydroxymethyl-6,6-dimethyl-bicyclo [3,3,1] hept-2-ene [(−)-myrtenol] (26 g), mercuric acetate (2.6 g) and ethyl vinyl ether (500 ml) is heated under reflux in an atmosphere of argon for 16 hours. On cooling, anhydrous potassium carbonate (4.5 g) is added and the excess ethyl vinyl ether is removed by distillation. The residue is filtered, the solid washed with hexane (2×20 ml) and the combined filtrate and washings are distilled to give the title compound as an oil (22 g, 72%), b.p. 105°–109° C./17 mm, ν$_{max}$(film) 2975, 2910, 2820 and 1605 cm$^{-1}$.

(2) 3-β-Formylmethyl-2-methylene-6,6-dimethyl-bicyclo [3,1,1] heptane

The vinyl ether (1) (2.0 g) is heated in a sealed tube at 200° C. for 7 hours. The resulting yellow oil is purified by chromatography on silica gel with toluene as eluant to give the title compound as an oil (1.4 g, 70%), ν$_{max}$(film) 1720 cm$^{-1}$.

In an alternative procedure which may produce higher yields, the vinyl ether (1) is passed in a stream of argon or nitrogen through a tube (1 cm × 10 cm) packed with glass wool and heated at 190° C., the product being condensed in a cold trap and distilled to give the title compound as an oil, b.p. 70°–75° C./1 mm.

(3) 3-β-(6'-Carboxyhex-2'Z-enyl)-2-methylene-6,6-dimethyl-bicyclo [3,1,1] heptane (4-Carboxy-n-butyl)triphenylphosphonium bromide (7.0 g) is dried at 75° C. under vacuum for 90 minutes, cooled and the flask released to dry nitrogen. Dry dimethyl sulphoxide (DMSO) (25 ml) is added, followed by the slow addition of 18 ml of a 1.6M solution of butyl-lithium in hexane. The temperature is held at 25° C. and the aldehyde (2) (1.5 g) in DMSO (5 ml) is added to the red ylid solution. The mixture is stirred overnight under nitrogen, then poured into 10% w/v aqueous sodium chloride (200 ml). The aqueous mixture is extracted with ether (3×75 ml), and the aqueous layer is then acidified to pH4 with 2N hydrochloric acid and re-extracted with ether (3×50 ml). The extracts of the acidified aqueous layer are dried over magnesium sulphate and evaporated to give the title compound as a yellow oil (2.0 g, 86%), δ(CDCl$_3$) 0.75 (s, 3H), 1.25 (s, 3H), 4.73 (m, 2H), 5.45 (m, 2H).

(4) 3-β-(6'-Methoxycarbonylhex-2'Z-enyl)-2-methylene-6,6-dimethyl-bicyclo [3,1,1] heptane The acid (3) (2.0 g) is treated with an ethereal solution of diazomethane (120 ml) and a few drops of methanol are added. The solution is stirred for 20 minutes and the solvent is then removed under vacuum to give the title compound as a yellow oil (2.2 g, 100%).

(5) 2-α-Hydroxymethyl-3-β-(6'-methoxycarbonylhex-2'Z-enyl)-6,6-dimethyl-bicyclo [3,1,1] heptane and 2-β-Hydroxymethyl-3-β-(6'-methoxycarbonylhex-2'Z-enyl)-6,6-dimethyl-bicyclo [3,1,1] heptane The ester (4) (0.92 g) is placed in a dry 100 ml round-bottomed flask under nitrogen and is treated at 0° C. over 5 minutes using magnetic stirring with 9-bora-bicyclo [3,3,1] nonane (a-BBN) in tetrahydrofuran (20 ml of 0.5M solution). The reaction mixture is stirred at room temperature for 3 hours, and then 3N aqueous sodium hydroxide (3.3 ml, 10 mmol) is added, followed by 30% v/v aqueous hydrogen peroxide (3.3 ml) over a period of 10 minutes, cooling being required to control the resulting exothermic reaction. The mixture is then stirred under air for 15 minutes, treated with potassium carbonate (3 g), and the organic upper layer separated off and dried over potassium carbonate. Evaporation of the solvent gives a cloudy yellow oil, which is stirred overnight in a 10:1 v/v toluene:light petroleum mixture (30 ml). The upper layer is decanted and evaporated to give a mixture of the title compounds as an oil (0.4 g, 41%), δ(CDCl$_3$) 0.92 (s) and 0.98 (s, total of 3H), 1.23 (s, 3H), 3.6–3.9 (m, 2H), 3.67 (s, 3H), 5.42 (m, 2H).

(6) 2-α-Formyl-3-β-(6'-methoxycarbonyl-hex-2'Z-enyl)-6,6-dimethyl-bicyclo [3,1,1] heptane and 2-β-formyl-3-β-(6'-methoxycarbonylhex-2'Z-enyl)-6,6-dimethyl-bicyclo [3,1,1] heptane The mixture of epimeric alcohols (5) (0.294 g) is dissolved in dry dichloromethane (1.5 ml) and pyridinium dichromate (0.6 g) is added. The mixture is stirred for 22 hours at room temperature and then dry ether (3 ml) and hexane (3 ml) are added. Stirring is continued for 15 minutes, and the mixture is then filtered. The last traces of the chromium salt are removed by passing the filtrate through anhydrous magnesium sulphate (5 g). Evaporation of the filtrate gives a mixture of the title compounds as an oil (0.075 g, 25.4%), $\delta(CDCl_3)$ 0.75 (s) and 0.96 (s, total of 3H), 1.21 (s, 3H), 3.67 (s, 3H), 5.42 (m, 2H), 9.70 (d) and 9.87 (d, total of 1H).

(7) 3-β-(6'-Carboxyhex-2'Z-enyl)-2-formyl-6,6-dimethyl-bicyclo [3,1,1] heptane

The aldehyde/ester (6) (0.075 g) is treated with 0.2N 5% v/v aqueous methanolic potassium hydroxide at 40° C. for 2 hours. The solution is then neutralized with 2N aqueous hydrochloric acid and extracted with ether (3×20 ml). The extracts are dried over magnesium sulphate and the solvent evaporated to give the title compound as an oil (0.065 g, 65%), $\delta(CDCl_3)$ 0.75 (s, 3H), 1.22 (s, 3H), 5.45 (m, 2H), 9.6 (br, 1H), 9.71 (s or finely split d, 1H).

This aldehyde/acid (7) is obtained as a compound having a 2-formyl substituent with either the α or β configuration. The formation of a single compound from the aldehyde ester (6) which is a mixture of compounds having a 2-formyl substituent with either an exo or an endo configuration is due to the epimerisation resulting from the use of the base to effect de-esterification. It has not been possible, however, to identify which of the two configurations should be assigned to the 2-formyl substituent of the aldehyde acid.

(8) 3-β-(6'-Carboxyhex-2'Z-enyl)-2-[N-(phenylcarbamoyl)-hydrazonomethyl]-6,6-dimethyl-bicyclo [3,1,1] heptane The acid/aldehyde (50 mg) is heated at 40° C. with phenylsemicarbazide [45 mg, prepared as described in Example 4(7)] in dioxane for 2 hours. The dioxane is removed in vacuo and the resulting product is chromatographed on Sephadex LH20 substituted by Nedox 1114 olefin oxide to 20% w/w, eluting with (all proportions by volume) 100 parts of hexane, 100 parts of 1,2-dichloroethane and 5 parts of ethanol with 0.1% of the total of glacial acetic acid. The chromatography gives the title compound as an oil (27 mg), $\lambda_{max}$ (CH$_3$OH) 246.5 nm, $\epsilon_{max}$ 16,000, $\delta(CDCl_3)$ 0.98 (s, 3H), 1.25 (s, 3H), 5.40 (m, 2H), 7.0–7.6 (m, 5H), 8.05 (br, 1H), 9.60 (br, 1H), M+ 411.

EXAMPLE 10 trans-4-(6'-Carboxyhex-2'Z-enyl)-5-(O-p-fluorobenzyloxyiminomethyl)-cyclohex-1-ene (1) cis-4,5-bis-Hydroxymethylcyclohex-1-ene A solution of the anhydride of 3,4-dicarboxycyclohex-1-ene (25.8 g) in THF (150 ml) is added with cooling to a stirred suspension of LiAlH$_4$ (9 g) in THF (200 ml) under N$_2$ at a rate such as to maintain the temperature at 0° C. After stirring for 18 hours at room temperature the mixture is gently refluxed for one hour and cooled in ice. The excess lithium aluminium hydride is decomposed by the careful addition of 1:1 THF-H$_2$O mixture (100 ml). After dilution with chloroform (150 ml) the resulting mixture is filtered and the solid is washed with chloroform (3×25 ml). Concentration of the filtrate under reduced pressure yields an oily residue which is dissolved in benzene, dried over (MgSO$_4$) and reconcentrated in vacuo to give the title compound as an oil (22 g, ca. 90%), $\nu_{max}$ (film) 3350 cm$^{-1}$.

(2) cis-4-Hydroxymethyl-5-benzyloxymethylcyclohex-1-ene

The diol (1) (16.2 g) in dimethylformamide (50 ml) is added dropwise to sodium hydride (3.1 g) in dimethylformamide (DMF) (50 ml). The mixture is stirred for 20 minutes and then benzyl chloride (16 g) is added and stirring is continued for a further 18 hours at 70° C. After removing the DMF in vacuo, water is added and the mixture is extracted with ether. The combined extracts are dried (MgSO$_4$) and the solvent is evaporated to give a residue which is distilled under reduced pressure to give the title compound as an oil (16.5 g, ca. 60%), b.p. 140°–145° C./0.03 mm, $\nu_{max}$ (film) 3440 and 1600 cm$^{-1}$.

(3) cis-4-p-Toluene-sulphonyloxymethyl-5-benzyloxymethyl cyclohex-1-ene

The alcohol/benzyl ether (2) (10 g) in 20 ml of dry pyridine is added slowly at 0° C. to p-toluenesulphonyl chloride (10.4 g) in pyridine (60 ml). The mixture is kept overnight at room temperature and is then quenched by pouring over crushed ice with vigorous shaking. The product is extracted with ether, washed consecutively with water, 0.1M sodium carbonate and brine, dried (MgSO$_4$), and concentrated in vacuo at room temperature. The crude product is purified on a silica gel column, eluting with benzene-ethyl acetate (95%:5% v/v) to give the title compound (14 g, 90%). The i.r. spectrum shows the absence of a hydroxyl group.

(4) cis-4-Cyanomethyl-5-benzyloxymethylcyclohex-1-ene

The p-toluene sulphonyl ester/benzyl ether (3) (12 g) in dimethylsulphoxide (DMSO) (15 ml) is added with stirring to potassium cyanide (3 g) in DMSO (20 ml). The mixture is heated at 100° C. under nitrogen for 6 hours and is then cooled, poured into water and the product extracted with ether. The solvent is removed and the residue purified on a Florisil column, eluting with petroleum ether-benzene (1:1) to give the title compound as an oil (6.5 g, ca. 80%) $\nu_{max}$ (film) 2220 and 1600 cm$^{-1}$.

(5) cis-4-Formylmethyl-5-benzyloxymethylcyclohex-1-ene

Di-isobutyl aluminium hydride (25 ml of a 1M solution in hexane) is added with stirring over a 15 minute period to the cyano/benzyl ether (4) (5.0 g) in dry toluene (70 ml) at −10° C. under N$_2$. After stirring for a further one hour at room temperature, the reaction is terminated by the cautious addition of methanol (6 ml), followed by saturated aqueous sodium hydrogen tartrate (95 ml). The mixture is then stirred and heated at 40° C. for 2 hours. The organic phase is separated and the aqueous layer is further extracted with ethyl acetate, the combined organic solutions being dried and the solvent evaporated to give an oil. Chromatography of the oil on Florisil, eluting with benzene gives the pure title compound as an oil (3.0 g 60%), $\nu_{max}$ (film) 1715 cm$^{-1}$.

(6) cis-4-(6'-Carboxyhex-2'Z-enyl)-5-benzyloxymethyl-cyclohex-1-ene (4-Carboxyl-n-butyl)-triphenylphosphonium bromide (7.0 g) is dried at 75° C. under vacuum for 2 hours. The white solid is cooled, the vacuum is released to dry nitrogen and DMSO (10 ml) is added followed by 9 ml of 2M solution of dimesyl sodium in DMSO. The temperature is maintained at 25° C. and the aldehyde/benzyl ether (5) (1.5 g) in DMSO is added to the deep red ylide solution. After stirring overnight the solvent is removed at 55°–60° C. under reduced pressure. The residue is dissolved in water, extracted with ether, and the aqueous phase carefully acidified to pH 4 with 2N HCl. The mixture is extracted with ether and the ethereal solution dried (MgSO$_4$) and concentrated in vacuo to give the title compound (10 g), $\nu_{max}$ (film) 1700 cm$^{-1}$.

(7) cis-4-(6'-Carboxyhex-2'Z-enyl)-5-hydroxymethylcyclohex-1-ene

To a stirred suspension of 1.5 g of the acid/benzyl ether (6) in 100 ml of liquid ammonia is added a total of 1 g of sodium in portions over 10–12 minutes at the end of which time the characteristic deep blue colour persists. The mixture is stirred for 30 minutes, the blue colour is then discharged by the careful addition of ammonium chloride and the reaction mixture is evaporated to dryness under a stream of nitrogen. The solid residue is triturated with 50 ml of benzene (to remove benzyl alcohol) and it is then dissolved in 40 ml of water. The aqueous solution is treated with Norit, then acidified with acetic acid and extracted with chloroform. Evaporation of the solvent gives the title compound as an oil (0.9 g), $\nu_{max}$ (film) 3350–3450 and 1700 cm$^{-1}$.

(8) cis-4-(6'-Ethoxycarbonylhex-2'Z-enyl)-5-hydroxymethylcyclohex-1-ene

The acid/alcohol (7) (0.75 g) is dissolved in ethanol, 0.3 ml of concentrated sulphuric acid is added and the mixture is heated under reflux for 18 hours. The mixture is then diluted with water and extracted with ether. The ethereal extracts are washed with water, saturated aqueous sodium bicarbonate and aqueous sodium chloride, and then dried (MgSO$_4$). Evaporation of the solvent gives the title compound as an oil (0.8 g), $\nu_{max}$ (film) 1725 cm$^{-1}$.

(9) trans-4-(6'-Ethoxycarbonylhex-2'Z-enyl)-5-formylcyclohex-1-ene

The ester/alcohol (8) (1.3 g), dicyclohexylcarbiimide (3.5 g) DMSO (5 ml) and dry benzene (10 ml) are placed in a 125 ml flask under nitrogen. Pyridinium trifluoroacetate (0.8 g) is added in one portion and the mixture is stirred for 18 hours. Ethyl acetate (50 ml) is added and the reaction mixture is then filtered. The filtrate is washed with water, saturated aqueous sodium chloride, and dried (Na$_2$SO$_4$). The solvent is evaporated to give a slurry residue which is redissolved in benzene. Solid particles separate from the solution and the solvent is then evaporated to give the title compound as an oil (1.0 g), $\nu_{max}$ (film) 1715 cm$^{-1}$, $\delta$(CDCl$_3$) 1.61–2.06 (m) 2.15–2.28 (t, 1H), 2.40 (t, 2H), 5.40 (m, 2H), 5.70 (s, 2H), 9.79 (d, 1H), M+ 250 (as methyl ester).

(10) trans-4-(6'-Carboxyhex-2'Z-enyl)-5-(O-p-fluorobenzyloxyiminomethyl)-cyclohex-1-ene The ester/aldehyde (9) (100 mg) is heated with p-fluorobenzyloxyamine hydrochloride (120 mg) in 5 ml pyridine for two hours at 60° C. The pyridine is removed in vacuo and the residue is partitioned between water of pH 4 and ether. The ethereal solution is dried (MgSO$_4$) and the solvent evaporated to give the title compound in the form of its ethyl ester as an oil. This ester is hydrolysed by heating in aqueous methanolic (2:1, CH$_3$OH/H$_2$O) 0.1N potassium hydroxide for three hours at 40° C. The mixture is diluted with water and extracted once with ether. The aqueous layer is then acidified to pH 4 and extracted with ether. Evaporation of the solvent gives the title compound as an oil, $\lambda_{max}$ (CH$_3$OH) 263 nm, $\epsilon_{max}$ 480, $\delta$(CDCl$_3$) 5.01 (s, 2H), 5.39 (m, 2H), 5.65 (m, 2H), 6.75 (d, 1H), 6.90–7.50 (m, 4H); M+ 387 (as methyl ester).

The p-fluorobenzyloxamine hydrochloride is prepared as follows.

N-Hydroxyphthalimide (12.0 g) in 130 ml dimethyl sulphoxide is treated with anhydrous finely divided potassium carbonate (6.6 g), when the dark red colour of the anion develops. The mixture is then treated dropwise at room temperature with p-fluorobenzyl chloride (20 g) and the mixture is stirred overnight or until the red colour is discharged. The reaction mixture is poured into water, and the resultant crystalline product is filtered off. Recrystallisation from ethanol gives N'-p-fluorobenzyloxyphthalimide in pure form as white needles. (16.4 g, 82%), m.p. 156°–157° C.

The imide (13.5 g) is boiled in 400 ml ethanol with 99% hydrazine hydrate (2.5 g) for two hours. The mixture is cooled, 7 ml of conc. hydrochloric acid is added and the precipitate of phthalhydrazide is removed by filtration. The solution is concentrated to dryness and the salt taken up in water, washed with ether and then basified. The free base is taken into ether to give an ethereal solution which is washed with brine and then dried (MgSO$_4$). Dry hydrogen chloride gas is passed into the ethereal solution to deposit pure p-fluorobenzyloxyamine hydrochloride which is recrystallised from ethanol as white plates (7.9 g, 90%), m.p. 298°–300° C.

EXAMPLE 11

1α-Hydroxy-2α-(6'-carboxyhex-2'Z-enyl)-3β-(O-diphenylmethyloxyiminomethyl)-cyclopentane (1) 6-(1',3'-Dioxacyclopent-2'-yl)-2-oxabicyclo [3,3,0] octane-3-one 6-Formyl-2-oxabicyclo [3,3,0] octane-3-one (2.0 g) is heated at 60° C. in benzene (50 ml) with ethylene glycol (1 ml) and a trace of toluene-p-sulphonic acid under a Dean and Stark head. When reaction ceases, the reaction mixture is cooled and treated with water (20 ml) and 10% w/v aqueous NaHCO$_3$ (20 ml). The organic phase is separated, washed with water, dried and concentrated to give the title compound in 95% yield, $\nu_{max}$ (film) 1750 cm$^{-1}$.

The starting material is prepared by the treatment of 1,3-cyclohexadiene with dichloroacetyl chloride, followed by dechlorination with zinc and acetic acid of the resulting adduct to give bicyclo [4,2,0]-oct-2-en-7-one. This compound is subjected to Baeyer-Villiger oxidation to give 7-oxabicyclo [4,3,0] non-2-en-8-one which is treated with thallium (III) nitrate under carefully controlled conditions to give 6-formyl-2-oxabicyclo [3,3,0] octane-3-one having properties identical with those reported by Corey and Ravindranathan, Tetrahedron Letters, 1971, 4753.

(2) 6-(1',3'-Dioxacyclopent-2'-yl)-3-hydroxy-2-oxabicyclo [3,3,0] octane

The lactone/acetal (1) (0.5 g) in dry toluene is cooled to −60° C. and treated under N$_2$ dropwise from a syringe with 2 ml of a 25% w/v solution of diisobutylaluminium hydride in toluene. The reaction is quenched at −60° C. after 2.5 hours by the careful addition of methanol (1 ml). The reaction mixture is then diluted with ether (50 ml) and is warmed to room temperature. Water (0.5 ml) is added and stirring is continued for 40 minutes followed by drying over anhydrous MgSO$_4$. Evaporation of the solvent in vacuo gives the title compound as an oil (0.42 g), $\nu_{max}$ (film) 3400 cm$^{-1}$.

(3) 1α-Hydroxy-2α-(6'-carboxyhex-2'Z-enyl)-3β-(1',3'-dioxacyclopent-2-yl)-cyclopentane Dimesyl sodium in DMSO (2.05 ml) is added dropwise to a solution of (4-carboxy-n-butyl)-triphenylphosphonium bromide (2.3 g) (dried before use) in 3 ml of DMSO. To the resultant red solution of the ylide is added dropwise a solution of the hydroxy/acetal (2) (0.5 g) in 5 ml of DMSO and the mixture is stirred overnight. The reaction mixture is then diluted with water (50 ml) and extracted with ethyl acetate. The cooled aqueous layer is acidified with dilute HCl to pH 4 and extracted with ethyl acetate. The organic extracts are washed with water, dried (MgSO$_4$) and concentrated. The resulting crude product is purified by chromatography on Unisil using toluene-ether (1:1 v/v) as eluant to yield the title compound as an oil (0.4 g), $\nu_{max}$ (film) 3350–3420 cm$^{-1}$.

(4) 1α-Hydroxy-2α-(6'-carboxyhex-2'Z-enyl)-3β-formylcyclopentane

The hydroxy/acid/acetal (3) (0.15 g) is hydrolysed by dissolving it in 20 ml of dioxane-water mixture (1:1 v/v) and heated at 40° C. with 0.05M aqueous HCl for 3 hours. 100 ml of water is added and the product extracted with ether. The solvent is evaporated and the residue purified by silica gel chromatography, eluting with a gradient from 10% v/v ethyl acetate in toluene to pure ethyl acetate, to give the title compound as an oil (95 mg), δ(CDCl$_3$) 4.30 (br, 1H), 5.40 (m, 2H), 6.70 (br, 1H), 9.60 (d, 1H).

(5) 1α-Hydroxy-2α-(6'-carboxyhex-2'Z-enyl)-3β-(O-diphenylmethyloxyiminomethyl)-cyclopentane The hydroxy/acid/aldehyde (4) (50 mg) is heated at 60° C. for 2 hours in pyridine (5 ml) with diphenylmethyloxyamine hydrochloride (70 mg, prepared by an analogous route to that described in Example 10 for p-fluorobenzyloxyamine hydrochloride). The pyridine is removed in vacuo and the residue partitioned between water (pH 4) and ether. The ethereal extract is dried and the solvent evaporated to give a residue which is purified by liquid-gel partition chromatography on a column of Sephadex LH20 substituted with Nedox 1114 olefinoxide to 20% w/w, eluting with hexane/dichloroethane/ethanol (100:100:5 v/v/v) containing 0.1% v/v of acetic acid, to give the title compound as an oil (32 mg), $\lambda_{max}$(CH$_3$OH) 258 nm, $\epsilon_{max}$590, δ(CDCl$_3$) 4.25 (br, 1H), 5.40 (m, 2H), 5.80 (br, 1H), 6.20 (s, 1H), 6.65 (d) and 7.50(d, 1H together), 7.30 (s, 10H): M+ not seen, M-167 and 167 [CH(C$_6$H$_5$)$_2$] prominent (as methyl ester).

EXAMPLE 12

5-endo-(6'-Carboxyhex-2'Z-enyl)-6-exo-O-[2'-(diphenylmethoxy)-ethyl]-oxyiminomethyl]-bicyclo [2,2,1] heptane 5-endo-(6'-Carboxyhex-2'Z-enyl)-6-exo-formyl-bicyclo [2,2,1] heptane [100 mg, prepared as described in Example 1 (9)] is heated at 60° C. for 2 hours in dry pyridine (5 ml) with a 50% excess of (2'-diphenylmethoxyethyl)-oxyamine hydrochloride. The pyridine is evaporated off in vacuo and the residue is partitioned between water (pH 4) and ether. The ether layer is dried (MgSO$_4$) and evaporated. The residue is chromatographed on Sephadex LH20 substituted by Nedox 1114 olefin oxide to 20% w/w, eluting with dichloroethane/hexane/ethanol (100:100:5 v/v/v) containing 0.1% v/v of acetic acid to give the title compound as an oil (101 mg), δ(CDCl$_3$) 3.70 (t, 2H), 4.20 (t, 2H), 5.30 (m, 2H), 5.40 (s, 1H), 6.50 (d, 1H), 7.30 (s, 10H), M+ 475 and M-167 (as methyl ester).

The (2'-diphenylmethoxyethyl)-oxyamine hydrochloride is prepared from 1-chloro-2-(diphenylmethoxy)-ethane in an analogous fashion to that described in Example 10 for p-fluorobenzyloxyamine hydrochloride.

EXAMPLE 13

5-endo-(6'-Carboxyhex-2'Z-enyl)-6-exo-[N-(dibenzylaminoacetyl)-hydrazonomethyl]-bicyclo [2,2,1] heptane 5-endo-(6'-Carboxyhex-2'Z-enyl)-6-exo-formyl-bicyclo [2,2,1] heptane (100 mg) is heated at 60° C. for two hours in ethanol with a 50% excess of (dibenzylaminoacetyl)-hydrazine. The solvent is evaporated off and the residue is chromatographed using the system described in Example 12 to give the title compound as an oil (129 mg), $\lambda_{max}$ (CH$_3$OH) 232 nm (shoulder), $\epsilon_{max}$ 10,270, and 215 nm (steep portion), $\epsilon_{max}$ 21,540, δ(CDCl$_3$) 3.25 (s, 2H), 3.65 (s, 2H), 5.35 (m, 2H), 7.30 (s, 10H), M 499 (loss of 2H).

The (dibenzylaminoacetyl)-hydrazine used in this Example is prepared as follows. Ethyl bromoacetate (8.35 g) in sodium dried benzene is added slowly to dibenzylamine (10.7 g) and the mixture stirred for three hours. The mixture is then filtered and the solvent removed to give a residue which is a mixture of the hydrobromide of dibenzylamine and the ethyl ester of dibenzylaminoacetic acid. These compounds are separated by differential crystallisation from ethanol, the hydrobromide, m.p. 227° C., crystallising from hot ethanol and the ester, m.p. 54.9° C. from ethanol at −20° C. after standing overnight. The ester (3 g) is added slowly to hydrazine (3 g) in dioxane and the mixture is refluxed. The (dibenzylaminoacetyl)-hydrazine crystallises from the mixture and is recrystallised from cold ether, m.p. 124.2° C.

EXAMPLE 14

5-endo-(6'-Carboxyhex-2'Z-enyl)-6-exo-(N-benzoxazol-2-yl-hydrazonomethyl)-bicyclo [2,2,1] heptane 5-endo-(6'-Carboxyhex-2'Z-enyl)-6-exo-formyl-bicyclo [2,2,1] heptane (100 mg) is heated at 60° C. for two hours in pyridine/dioxane with benzoxazol-2-yl hydrazine hydrochloride (150 mg). The solvent is then evaporated in vacuo and the residue is partitioned between water (pH 4) and ether. The ether layer is dried (MgSO$_4$) and evaporated. The residue is chromatographed using the system described in Example 2(1) to give the title compound as an oil (32.4 mg), $\lambda_{max}$ (CH$_3$OH) 255 nm, $\epsilon_{max}$ 13,700, and 285 nm, $\epsilon_{max}$ 18,400, δ(CDCl$_3$) 5.49 (m, 2H), 6.60 (d, 1H), 7.0–7.5 (m, 4H), M+ 381 and also M-127.

The benzoxazol-2-yl-hydrazine hydrochloride used in this Example is prepared from 2-chlorobenzoxazole b.p. 80°–2° C./15 mm, which is in turn prepared from 2-mercaptobenzoxazale by the procedure described in the Journal of the Chemical Society, 1965, 4393. The 2-chlorobenzoxazale is heated in dioxane for two hours with an equimolar proportion of hydrazine and the benzoxazol-2-yl hydrazine hydrochloride is precipitated by the addition of ether to the reaction mixture.

EXAMPLE 15

5-endo-(6'-Carboxyhex-2'Z-enyl)-6-exo-(N-p-toluenesulphonylhydrazonomethyl)-bicyclo [2,2,1] heptane 5-endo-(6'-Carboxyhex-2'Z-enyl)-6-exo-formyl-bicyclo [2,2,1] heptane (100 mg) is heated at 60° C. for two hours in tetrahydrofuran (5 ml) with p-toluene sulphonyl hydrazide. The solvent is evaporated in vacuo and the residue is chromatographed on Unisil (10 g) using as eluant a gradient from 10% ethyl acetate in benzene to pure ethyl acetate to give the title compound as an oil (50 mg), $\lambda_{max}$ (CH$_3$OH) 227 nm, $\epsilon_{max}$ 11,900, $\delta$(CDCl$_3$) 2.40 (s, 3H), 5.25 (m, 3H), 6.55 (d) and 7.15 (d, 1H together), 7.30 (m) and 7.80 (m, 4H together).

The p-toluene sulphonyl hydrazide used in this Example is prepared by reacting p-toluene sulphonyl chloride with hydrazine hydrate.

EXAMPLE 16

5-endo-(6'-Carboxyhex-2'Z-enyl)-6-exo-(N-(diphenylmethyl)-azinomethyl]-bicyclo [2,2,1] heptane 5-endo-(6'-Carboxyhex-2'Z-enyl)-6-exo-formyl-bicyclo [2,2,1] heptane (100 mg) is heated at 40° C. for two hours in ethanol (5 ml) with benzophenone hydrazone (100 mg). The solvent is then evaporated in vacuo and the residue is chromatographed using the system described in Example 12 to give the title compound as an oil (106 mg), $\lambda_{max}$ (CH$_3$OH) 243 nm, $\epsilon_{max}$ 11,240, and 270 nm, $\epsilon_{max}$ 12,200, $\delta$(CDCl$_3$) 5.30 (m, 2H), 7.2–7.80 (m, 10H).

The benzophenone hydrazone used in this Example is prepared by reacting refluxing benzophenone in ethanol with a 3-molar excess of hydrazine hydrate for three hours, then cooling the reaction mixture to −20° C. to crystallise the hydrazone, m.p. 99.1° C.

EXAMPLE 17

Further compounds

The additional compounds of formula (I) listed in Table 1 below are prepared by analogous procedures to those described in previous examples; the semicarbazone and thiosemicarbazone derivatives, for example, being obtained through reaction with an approximately 50% molar excess of the appropriate reagent RNH$_2$ for two hours at 40° C. In Table 1 the melting point of the individual reagents RNH$_2$ is given together with the amount of aldehyde or ketone intermediate used and the amount of the compound (I) which is obtained. The solvent used for the reaction is dioxane in the case of compounds 1, 6, 9 and 10; tetrahydrofuran in the case of compounds 2 and 3; ethanol in the case of compounds 4, 5, 7, 8; and pyridine in the case of compound 11.

Each of the compounds contains an unmodified 6-carboxyhex-2 Z-enyl group. However, the free acids, in the case of these compounds and also those described in previous examples, are convertible to the methyl esters by solution in methanol, using warming and addition of NaHCO$_3$ as necessary, followed by the addition of an excess of ethereal diazomethane to the methanolic solution, standing, and the removal of solvent. Physical data on the compounds are presented in Tables 2 and 3, U.V., M.S., and N.M.R. data being given for compounds 2, 3, 10 and 11 and analysed N.M.R. data for the remaining semicarbazone and thiosemicarbazone derivatives. The U.V. data is for a methanolic solution and the N.M.R. data is given as $\delta$ values relating to a CDCl$_3$ solution, referred to (CH$_3$)$_4$Si.

TABLE 1

| No. | (structure) | R$^2$ | R | Mp of RNH$_2$ °C. | Starting Material/ Product (mg/mg) |
|---|---|---|---|---|---|
| 1 | | H | —NHCSNHC$_6$H$_5$ | 133.7 | 100/92 |
| 2 | | | (benzothiazole N-methyl) | 144.2$^{(1)}$ | 100/87 |
| 3 | | | (fluorenylidene) | 159.6 | 100/87 |

TABLE 1-continued

| No. | Compound 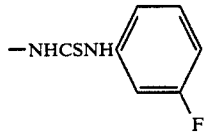 | R² | R | Mp of RNH₂ °C. | Starting Material/ Product (mg/mg) |
|---|---|---|---|---|---|
| 4 | 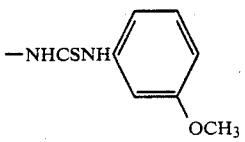 | CH₃ | —NHCSNH—⟨C₆H₄⟩—F | 158.7[2] | 100/85 |
| 5 | | | —NHCSNH—⟨C₆H₄⟩—OCH₃ | 158.7 | 80/87 |
| 6 | | | —NHCSNH—⟨C₆H₄⟩—OCH₃ | 149.8 | 50/32 |
| 7 | | | —NHCSNH—⟨C₆H₄⟩—CF₃ | 114.1 | 80/94 |
| 8 | 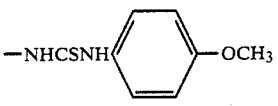 | CH₃ | —NHCONH—⟨C₆H₄⟩—OCH₃ | 210.3 | 100/102 |
| 9 | | | —NHCSNH—⟨pyridyl-N⟩ | 158.5 | 100/32 |
| 10 | 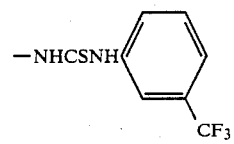 | H | —NHCSNHC₆H₅ | 133.7 | 50/56 |
| 11 | 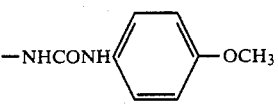 OH | H | —OCH₂—⟨C₆H₄⟩—F | 156–157 as HCl salt | 100/77 |

TABLE 2

| Compound No. | UV Data λmax | εmax | MS Data M⁺ | NMR Data (CDCl₃) |
|---|---|---|---|---|
| 2 | 226 | 25,070 | 411 | 3.50 (s,3H), 5.40 (m, 2H), |
|   | 311 | 17,830 |     | 6.8–7.4 (m, 4H), 7.70 (d, 1H) |
| 3 | 259 | 54,500 | 426 | 5.40 (m, 2H), 7.2–8.0 (m, 8H) |
|   | 310 | 15,300 |     |   |
| 10 | 274.5 | 25,800 | (1) | 5.35 (m, 2H), 5.70 (m, 2H), |
|    |       |        |     | 7.2–7.7 (m, 5H), 9.05 (br, 1H), |
|    |       |        |     | 10.30 (br, 1H) |
| 11 | 263 | 870 | 449[2] | 4.25 (br, 1H), 5.0 (s, 2H), |
|    |     |     |        | 5.30 (m, 2H), 6.60 (d, 1H), |

TABLE 2-continued

| Compound No. | UV Data λmax | εmax | MS Data M⁺ | NMR Data (CDCl₃) |
|---|---|---|---|---|
|   |   |   |   | 6.9–7.5 (m, 4H) |

Footnotes (Table 2)
[1] M⁺ not seen, intense ion at m/e 135 arising from C₆H₅CNS.
[2] On methyl ester.

TABLE 3

| Compound No. | Olefinic protons of $R^1$ | $R^2$ proton(s) | NH protons | Aromatic protons | Protons of aromatic substituent |
|---|---|---|---|---|---|
| 1 | 5.40 (m) | 6.45 (d) | 9.05 (br) 10.30 (br) | 7.2–7.7 (m) | — |
| 4 | 5.35 (m) | 2.0 (s) | 8.90 (br) 9.35 (br) | 6.8–7.8 (m) | — |
| 5 | 5.35 (m) | 1.98 (s) | 8.80 (br) 9.30 (br) | 6.7–7.6 (m) | 3.83 (s) |
| 6 | 5.30 (m) | 1.95 (s) | 8.80 (br) 9.20 (br) | 6.8–7.5 (m) | 3.80 (s) |
| 7 | 5.38 (m) | 2.0 (s) | 8.95 (br) 9.45 (br) | 7.4–8.0 (m) | — |
| 8 | 5.40 (m) | 1.90 (s) | 8.20 (br) 9.70 (br) | 6.8–7.5 (m) | 3.80 (s) |
| 9 | 5.40 (m) | 1.90 (s) | 9.0 (br) 9.8 (br) | 7.3–8.8 (m) | — |

EXAMPLE 18

In vitro tests of biological activity

Various of the compounds of formula (I) described in the Examples were tested for biological activity in the rabbit aorta and human platelet systems. The compounds, and the results obtained in each case, are shown in Table 4, all of the compounds tested containing an unmodified 6-carboxyhex-2'Z-enyl group.

Rabbit Aorta System

Spiral strips of thoracic aorta are suspended in Kreb's-Henseleit solution and aerated with 95% $O_2$/5% $CO_2$ at 37° C. Tension changes are recorded with a Glass FTO3 force transducer. Initially, cumulative dose response curves to 11,9-(epoxymethano) $PGH_2$ ($2\times10^{-9}$, $1\times10^{-8}$, $5\times10^{-8}$ and $2.5\times10^{-7}$M) are obtained. In a second experiment the individual compounds are added 30 minutes previous to the addition of the series of agonist doses. In the case of each compound, the affinity constant, $K_B$, for the compound is calculated according to the Gaddum - Schild Equation (based on Law of Mass Action).

$$DR - 1 = [B] \times K_B$$

DR = dose ratio

[B] = molar concentration of compound

Human Platelet System

Platelet-rich plasma is obtained from fresh, citrated human blood. Addition of the 11,9-(epoxymethano) $PGH_2$ ($1\times10^{-7}$ to $5\times10^{-7}$M) causes immediate aggregation recorded as an increase in light transmission (600 nm). In a second experiment the individual compounds are added five minutes previous to the addition of the $PGH_2$ analogue. The dose of the $PGH_2$ analogue added is then increased to a level which gives a similar response to that obtained in the absence of antagonist. The affinity constant, $K_B$, for the compound is calculated according to the Gaddum - Schild Equation (based on Law of Mass Action).

$$DR - 1 = [B] \times K_B$$

DR = dose ratio

[B] = molar concentration of compound

TABLE 4

| Compound | | | Affinity Constants × $10^{-6}$ (M$^{-1}$) | |
|---|---|---|---|---|
| (norbornane structure) | $R^2$ | R | Rabbit Aorta | Human Platelets |
| | H | —NHCSNH—(phenyl) | 1.9 | 3.8 |
| | H | —NHCSNHCH$_2$—(phenyl) | 1.9 | 0.78 |
| | CH$_3$ | —NHCSNH—(phenyl) | 11 | 20 |
| | CH$_3$ | —NHCSNH—(phenyl-F) | 14.2 | 22 |

TABLE 4-continued

| | R² | R | Affinity Constants × $10^{-6}$ ($M^{-1}$) Rabbit Aorta | Affinity Constants × $10^{-6}$ ($M^{-1}$) Human Platelets |
|---|---|---|---|---|
| | CH₃ | —NHCSNH—C₆H₄—OCH₃ (ortho) | 10.5 | 8.5 |
| | CH₃ | —NHCSNH—C₆H₄—OCH₃ (para) | 4.7 | 9.8 |
| | CH₃ | —NHCSNH—C₆H₄—CF₃ (meta) | 8.5 | 5.3 |
| | C₂H₅ | —NHCSNH—C₆H₅ | - | 3.9 |
| (bicyclic structure) | H | —NHCONH—C₆H₅ | 1.2 | (1) |
| | CH₃ | —NHCONH—C₆H₄—OCH₃ | 18 | 18 |
| | CH₃ | —NHCSNH—C₆H₅ | 12 | 21 |
| | CH₃ | —NHCSNH-pyridyl | 3.9 | 1.5 |
| (pinane structure with CH₃, CH₃) | H | —NHCSNH—C₆H₅ | 0.6 | 0.35 |
| | CH₃ | —NHCONH—C₆H₅ | 2.8 | 1.1 |

TABLE 4-continued

Compound

| R² | R | Affinity Constants × $10^{-6}$ (M$^{-1}$) Rabbit Aorta | Human Platelets |
|---|---|---|---|
| H (3,3-dimethylbicyclic) | —NHCONH—C₆H₅ | 3.0 | 0.50 |
| H (cyclohexene) | —NHCSNH—C₆H₅ | 0.91 | 2.0 |
| H (bicyclic) | —N=C(S)(N-CH₃) (methylbenzothiazoline) | 0.66 | 0.29 |
| H | —N=fluorenylidene | (2) | |
| H | —N=C(C₆H₅)₂ | 1.5 | (2) |
| H | —NH—(benzoxazol-2-yl) | 2.0 | 0.18 |
| H | —NHCOCH₂N(CH₂C₆H₅)₂ | 1.2 | — |
| H | —NHSO₂—C₆H₄—CH₃ | 2.9 | 1.5 |
| H | —OCH₂CH₂OCH(C₆H₅)₂ | 0.10 | 0.23 |

TABLE 4-continued

| Compound | | Affinity Constants × $10^{-6}$ ($M^{-1}$) | |
|---|---|---|---|
|  | | | |
| $R^2$ | R | Rabbit Aorta | Human Platelets |
| 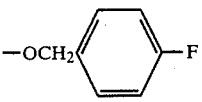 H | —OCH$_2$—⟨phenyl⟩—F | 2.6 | 0.12 |
| 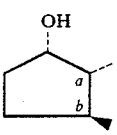 OH, H | —OCH$_2$—⟨phenyl⟩—F | 0.40 | — |
| 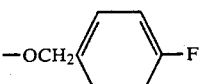 H | 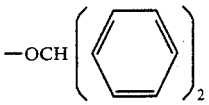 —OCH(phenyl)$_2$ | — | (2) |

(1) A hyphen indicates that the particular test was not carried out on the compound in question.
(2) An accurate value could not be obtained for these compounds as total inhibition occurred above a certain value; in addition the action of ADP on human platelets is also blocked.

EXAMPLE 19

In vivo Tests of Biological Activity (1) Inhibition of Platelet Aggregation

The technique employed in this test was basically that of Smith and Freuler, Bibl. anat., 1973, 12, 229–234, which utilises the Technicon Autocounter and provides a completely automated system for counting platelets and cells. Blood is continuously sampled from a suitable artery and to avoid the use of an anticoagulant, a double cannula is used which enables 3.8%, w/v aqueous trisodium citrate to be pumped to the tip of the cannula and the citrated blood then to be removed at 0.1 ml/minute and diluted in the manifold where the red cells are lysed with 1% w/v ammonium oxalate/0.002% w/v saponin solution. The platelets are then counted optically and the count continuously recorded on precalibrated chart paper.

(a) Tests in Rats

Each of a group of six male Sprague-Dawley rats anaesthetised with pentabarbitone was injected intravenously with 40 μg/kg of collagen followed, 15 minutes later, by 80 μg/kg of collagen, which gives a dose-dependent and reproducible fall in platelet count. Ten minutes after the second injection of collagen, the rats were treated intravenously with a dose of 1 mg/kg of 5-endo-(6'-carboxyhex-2'Z-enyl)-6-exo-{1'-[N-(phenylthiocarbamoyl)-hydrazono]ethyl}-bicyclo [2,2,1] heptane prepared as described in Example 2. At 5 and 20 minutes after the administration of this compound a further 40 μg/kg and 80 μg/kg of collagen, respectively, were administered. The levels of platelet aggregation resulting from the administration of the collagen before and after the administration of the bicyclo [2,2,1] heptane were recorded continuously as indicated above.

The responses, calculated as the percentage fall in the platelet count, to the administration of the two doses of collagen before and after administration of the bicyclo [2,2,1] heptane are shown in Table 5, the average response to 40 μg/kg collagen being significantly reduced [one tailed paired t-test gives t=2.25 (5Df), P<0.05], as is the average response to 80 g/kg collagen (t=2.86 (5Df), P<0.02).

TABLE 5

| | Percentage Fall in platelet count on administering collagen | | | |
|---|---|---|---|---|
| | Before Collagen μg/kg | | After Collagen μg/kg | |
| Rat No. | 40 | 80 | 40 | 80 |
| 1 | 21.5 | 38.3 | 14.0 | 18.3 |
| 2 | 20.3 | 27.7 | 13.3 | 27.1 |
| 3 | 28.5 | 42.8 | 14.6 | 28.4 |
| 4 | 35.4 | 48.5 | 25.0 | 34.4 |
| 5 | 16.7 | 35.9 | 18.5 | 34.5 |
| 6 | 17.7 | 33.5 | 19.4 | 28.2 |
| X̄ | 23.35 | 37.78 | 17.47 | 28.5 |
| SE± | 2.95 | 2.97 | 1.82 | 2.45 |

(b) Tests in Guinea Pigs

In three experiments, each conducted on one male albino guinea pig (400–10,000 g) anaesthetised with a mixture of allyl barbituric acid and urethane, the guinea pig was given intravenously a dose of 50 μg/kg of collagen, followed 15 minutes later by 0.35 μg/kg of 11,9-(epoxymethane) PGH$_2$ to give two reliable platelet aggregation responses for each material. After a further period of 10 minutes, the guinea pig was treated intravenously with a dose of 1 mg/kg of 5-endo-(6'-carboxyhex-2'Z-enyl)-6-exo{1'-[N-(phenylthiocarbamoyl)hydrazono]-ethyl}-bicyclo [2,2,1] heptane prepared as described in Example 2. Commencing 5 minutes after the administration of the bicyclo [2,2,1] heptane, the alternate treatments at 15 minute intervals with collagen and 11,9-(epoxymethano) PGH$_2$ were repeated, the second treatment with the latter compound being followed after 15 minutes by a final treatment with collagen. (In the first experiment, only, the last administration of each compound was omitted).

The level of platelet aggregation was recorded continuously throughout the experiment as described above. The administration of the bicyclo [2,2,1] heptane caused an inhibition of the platelet aggregation produced by both the collagen and the 11,9-(epoxymethano) $PGH_2$, the results being summarised in Table 6 which shows the percentage inhibition produced by the bicyclo [2,2,1] heptane in each of the responses to collagen and to the $PGH_2$ derivative obtained after administration of the drug. In the Table each figure corresponds to inhibition of either a collagen or $PGH_2$ derivative initiated response, as shown, the former material being administered at 5, 35 and 65 minutes after administration of the drug and the latter at 20 and 50 minutes thereafter.

The same three experiments on guinea pigs described under 1(b) are used to give a measure in a modified Konzett-Rossler test of the inhibition produced by 5-endo-(6'-carboxyhex-2'Z-enyl)-6-exo{1'[N-(phenylthiocarbamoyl)-hydrazono]ethyl}-bicyclo [2,2,1] heptane, prepared as described in Example 2, of the bronchoconstriction resulting from administration of the collagen and the $PGH_2$ derivative. This test involves artificially respiring the animals and measuring the amount of residual air with a pressure transducer. The collagen and $PGH_2$ derivative given prior to the bicyclo [2,2,1] heptane were each found to cause bronchoconstriction as shown by an increase in insufflation pressure but when this pressure was again measured 5 minutes after the administration of the bicyclo [2,2,1] heptane it was found in each instance that a complete inhibition of the bronchoconstricting effect had been produced by this compound.

TABLE 6

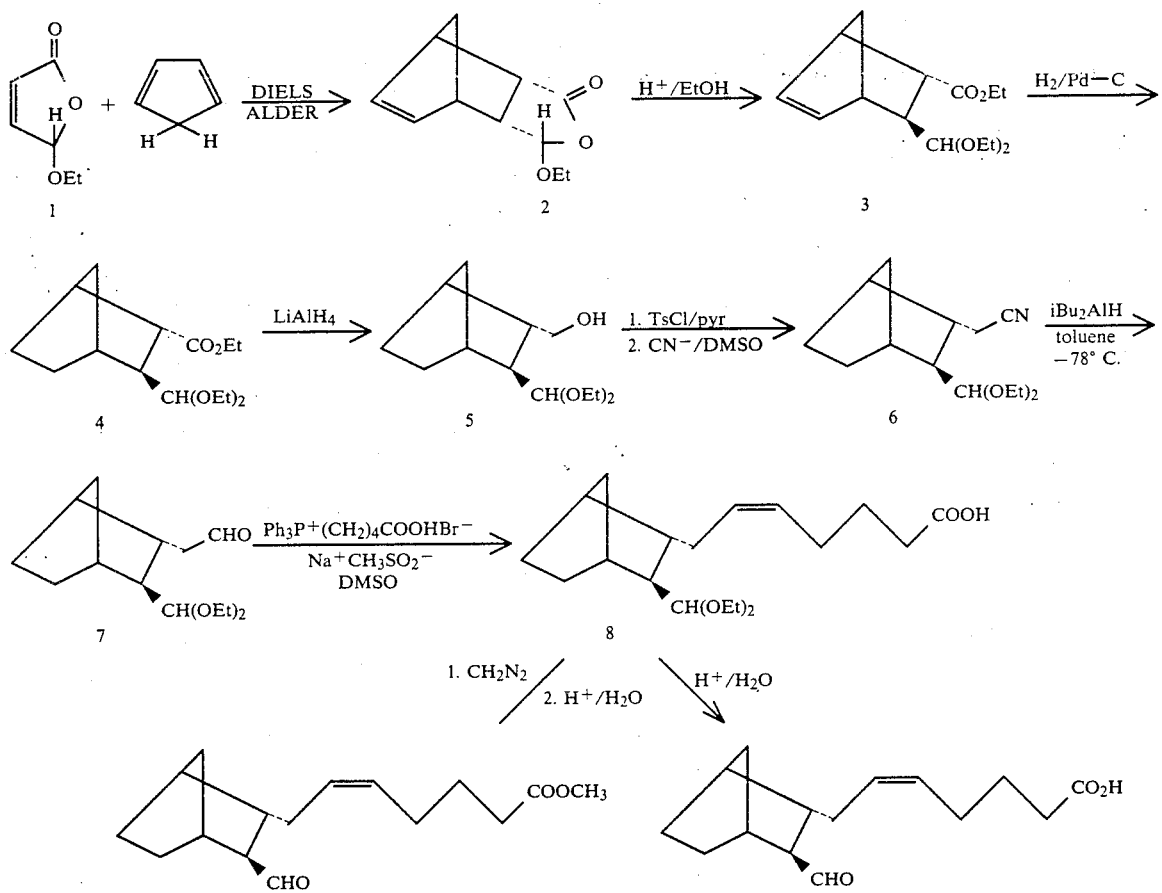

| Platelet Aggregator | Aggregator (μg/kg) | [2,2,1] Heptane (μg/kg) | after administration of drug | | | | |
| --- | --- | --- | --- | --- | --- | --- | --- |
| | | | 5 min | 20 min | 35 min | 50 min | 65 min |
| Collagen | 50 | 1 | 73.6 | | 67.3 | | — |
| $PGH_2$ deriv. | 0.35 | 1 | | 75.7 | | — | |
| Collagen | 50 | 1 | 64.5 | | 64.4 | | 56.1 |
| $PGH_2$ deriv. | 0.35 | 1 | | 85.2 | | 65.5 | |
| Collagen | 50 | 1 | 68.3 | | 56.1 | | 51.5 |
| $PGH_2$ deriv. | 0.35 | 1 | | 83.7 | | 64.6 | |
| Average | | | 68.8 | 81.5 | 62.6 | 65.1 | 53.8 |

(2) Inhibition of Bronchoconstriction

We claim:
1. A compound of formula

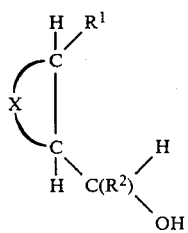

wherein

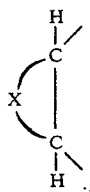

is one of the divalent cyclic groups

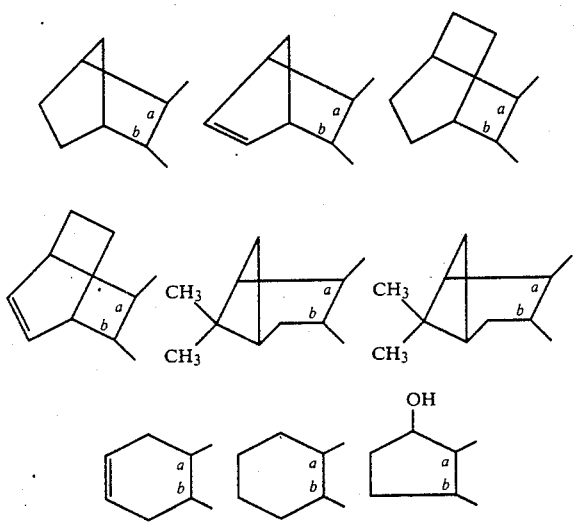

the letters a and b indicating in each case the points of attachment of the substituents $R^1$ and $C(R^2)HOH$ respectively;

$R^1$ is a group of the formula R'—COQ where R' is selected from the group consisting of —$(CH_2)_j$— where j is an integer from 4 to 8; —CH=CH—$(CH_2)_k$—, where k is 2 or 3; —$CH_2$—CH=CH—$(CH_2)_m$—, where m is an integer from 1 to 5; —$CH_2$—$CH_2$—CH=CH—$(CH_2)_n$—, where n is 0 or an integer from 1 to 4; —X—$(CH_2)_p$, where p is an integer from 3 to 7; —$CH_2$—X—$(CH_2)_q$—, where q is an integer from 2 to 6; and —$CH_2$—$CH_2$—X—$(CH_2)_m$—, where X is O or S; and COQ is carboxy, a physiologically acceptable carboxylate salt, a $C_1$-$C_5$ alkyl ester or $CONHSO_2CH_3$; and $R^2$ is selected from the group consisting of $C_{1-10}$ aliphatic hydrocarbon groups and $C_{1-10}$ aliphatic hydrocarbon groups substituted by Ar, OAr or SAr, where Ar represents a phenyl, naphthyl, fluorenyl, dibenzocyclohexyl, dibenzocycloheptyl, pyridyl, benzthiazolyl, dihydrobenzthiazolyl, N-methyldihydrobenzthiazolyl, benzoxazolyl, dihydrobenzoxazolyl or N-methyldihydrobenzoxazolyl group or such a group substituted by one or more substituents selected from $C_{1-10}$ alkoxy, halogen, $C_{1-10}$ halogen-substituted alkyl, sulphamoyl, amino, hydroxyl, nitro and $C_{1-10}$ alkyl groups.

2. A compound according to claim 1 which contains a bicyclo [2,2,2] octane or bicyclo [2,2,2] oct-2Z-ene ring system.

3. A compound according to claim 1 which contains a 6,6-dimethylbicyclo [3,1,1] heptane ring system having the group $R^1$ at the 3-position.

4. A compound according to claim 1, in which j is an integer from 5 to 7; k is 3; m is an integer from 2 to 4; n is an integer from 1 to 3; p is an integer from 4 to 6; and q is an integer from 3 to 5.

5. A compound according to claim 1, in which $R^1$ is (Z—)$CH_2$—CH=CH—$CH_2$—$CH_2$—$CH_2$—COQ.

6. A compound according to claim 1, in which $R^1$ is $CH_2$—$CH_2$—$CH_2$—$CH_2$—$CH_2$—$CH_2$—COQ.

7. A compound according to claim 1, in which COQ is COOH or a $C_1$-$C_5$ alkyl ester.

8. A compound according to claim 1, in which $R^2$ is a $C_{1-10}$ aliphatic hydrocarbon group.

9. A compound according to claim 1, in which $R^2$ is a $C_{1-3}$ alkyl group.

10. A compound according to claim 1, in which $R^2$ is ethyl.

11. A compound according to claim 1, in which $R^2$ is methyl.

12. A compound according to claim 1 in which the substituent $R^1$ is a group (Z—)—$CH_2$—CH=CH—$CH_2$—$CH_2$—$CH_2$—COQ or $CH_2$—$CH_2$—$CH_2$—$CH_2$—$CH_2$—$CH_2$—COQ and the substituent $C(R^2)HOH$ is a group wherein $R^2$ is methyl or ethyl.

13. A compound according to claim 1, in which the configuration about any double bond in the group $R^1$ is cis.

14. A compound according to claim 1, in which the groups $R^1$ and $C(R^2)HOH$ are in a trans relationship.

15. A compound according to claim 14, in which the divalent cyclic group has the 5-endo, 6-exo configuration when it is a bicyclo [2,2,2] oct-2Z-ene, and the the 2α, 3β, 6α configuration when it is a 6,6-dimethyl-bicyclo [3,1,1] heptane.

16. A compound according to claim 1 being trans-5-(6'-carboxyhex-2'Z-enyl)-6-(1'-hydroxyethyl)-bicyclo [2,2,2] octane or a $C_1$-$C_5$ ester thereof.

17. A compound according to claim 1 being 5-endo-(6'-carboxyhex-2'Z-enyl)-6-exo-(1'-hydroxyethyl)-bicyclo [2,2,2] oct-2Z-ene or a $C_1$-$C_5$ alkyl ester thereof.

18. A compound according to claim 1 being 2α-(6'-carboxyhex-2'Z-enyl)-3β-(1'-hydroxyethyl)-6,6-dimethyl-bicyclo [3,1,1] heptane or a $C_1$-$C_5$ alkyl ester thereof.

19. A compound according to claim 1 being 3β-(6'-carboxyhex-2'Z-enyl)-2-(1'-hydroxyethyl)-6,6-dimethyl-bicyclo [3,1,1] heptane or a $C_1$-$C_5$ alkyl ester thereof.

* * * * *